US011574284B2

(12) United States Patent
DeBusk et al.

(10) Patent No.: US 11,574,284 B2
(45) Date of Patent: *Feb. 7, 2023

(54) SYSTEM FOR PREVENTION OF FRAUD IN ACCOUNTING FOR UTILIZATION OF MEDICAL ITEMS

(71) Applicant: DeRoyal Industries, Inc., Powell, TN (US)

(72) Inventors: Brian C. DeBusk, Knoxville, TN (US); Joe L. Smith, Powell, TN (US); Mary E. Kaylor, Chattanooga, TN (US); Michael R. McBee, Knoxville, TN (US)

(73) Assignee: DeRoyal Industries, Inc., Powell, TN (US)

( * ) Notice: Subject to any disclaimer, the term of this patent is extended or adjusted under 35 U.S.C. 154(b) by 216 days.

This patent is subject to a terminal disclaimer.

(21) Appl. No.: 17/146,770

(22) Filed: Jan. 12, 2021

(65) Prior Publication Data

US 2021/0233015 A1    Jul. 29, 2021

Related U.S. Application Data

(63) Continuation of application No. 15/813,208, filed on Nov. 15, 2017, now Pat. No. 10,922,647, which is a
(Continued)

(51) Int. Cl.
*G06Q 10/08*     (2012.01)
*G06Q 10/087*    (2023.01)
(Continued)

(52) U.S. Cl.
CPC ....... *G06Q 10/087* (2013.01); *G06K 7/10316* (2013.01); *G06Q 50/22* (2013.01);
(Continued)

(58) Field of Classification Search
CPC .. G06Q 10/087; G06Q 50/22; G06K 7/10316; G16H 10/60; G16H 20/40; G16H 40/20; G16H 40/40
See application file for complete search history.

(56) References Cited

U.S. PATENT DOCUMENTS

2004/0046020 A1    3/2004  Andreasson et al.
2010/0141457 A1*   6/2010  Wass ............... G06Q 50/28
                                                    340/572.8
(Continued)

FOREIGN PATENT DOCUMENTS

WO    WO-2010056287 A1 *  5/2010  ........... G06F 19/366

OTHER PUBLICATIONS

"Digital Angel's VeriTeQ Gets Order for Its Q Inside Implantable Microchip." Entertainment Close-up: NA. Close-Up Media, Inc. (Aug. 19, 2013) (Year: 2013).*
(Continued)

*Primary Examiner* — Linh Giang Le
(74) *Attorney, Agent, or Firm* — Luedeka Neely Group PC

(57) ABSTRACT

At the time of manufacture of medical items that are to be consumed during patient care, a unique identification number is assigned to each item and the number is encoded in an RFID tag attached to the item. The manufacturer registers the unique identification number for each individual medical item in a Unique Device Identification (UDI) Serialized Tracking Database. The UDI Serialized Tracking Database maps each unique identification number to each item's UDI number that has been assigned by the Food and Drug Administration. As each item is consumed during medical treatment and its cost is billed to payers, the unique identification number of the item is reported and verified. This provides for detection of certain types of fraud in the
(Continued)

dispensing of medical items by validating that necessary supplies were actually used during patient care.

9 Claims, 15 Drawing Sheets

Related U.S. Application Data continuation of application No. 14/587,424, filed on Dec. 31, 2014, now Pat. No. 10,152,688, which is a continuation-in-part of application No. 14/504,859, filed on Oct. 2, 2014, now Pat. No. 9,922,304.

(60) Provisional application No. 62/422,295, filed on Nov. 15, 2016, provisional application No. 62/048,921, filed on Sep. 11, 2014, provisional application No. 61/993,578, filed on May 15, 2014, provisional application No. 61/900,064, filed on Nov. 5, 2013, provisional application No. 62/007,601, filed on Jun. 4, 2014.

(51) Int. Cl.
*G16H 40/40* (2018.01)
*G06K 7/10* (2006.01)
*G16H 20/40* (2018.01)
*G06Q 50/22* (2018.01)
*G16H 40/20* (2018.01)
*G16H 10/60* (2018.01)

(52) U.S. Cl.
CPC ............. *G16H 10/60* (2018.01); *G16H 20/40* (2018.01); *G16H 40/20* (2018.01); *G16H 40/40* (2018.01)

(56) References Cited

U.S. PATENT DOCUMENTS

| | | | |
|---|---|---|---|
| 2013/0088354 A1* | 4/2013 | Thomas | A61B 90/98 340/572.1 |
| 2014/0048593 A1 | 2/2014 | Hoganson | |

OTHER PUBLICATIONS

Anna-Marie Vilamovska, Improving the quality and cost of health care delivery; The potential of radio frequency identification (RFID) technology; The Pardee RAND Graduate School ProQuest Dissertations Publishing, 2010 (Year: 2010).

Ahmed Gamaleldin, RFID in Retail Stores and B2B Supply Chains, A Master's Thesis, Mar. 16, 2009, Long Island University, Brooklyn Campus, USA.

* cited by examiner

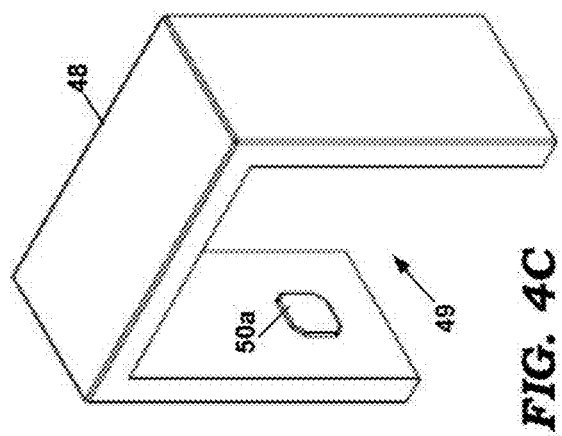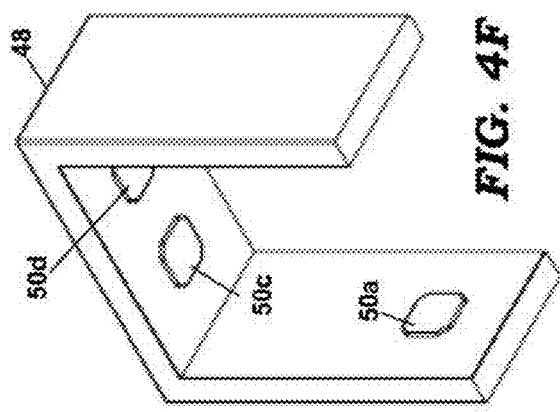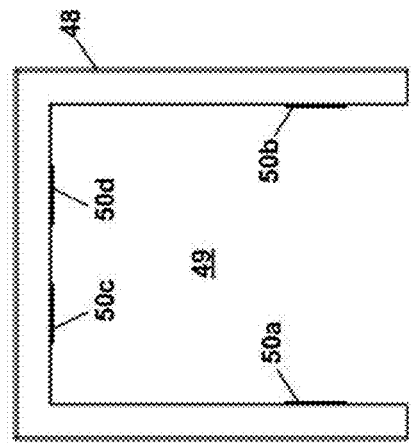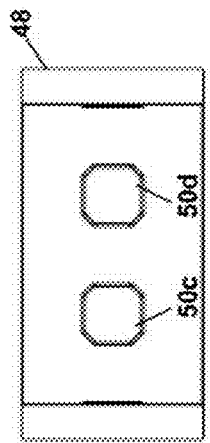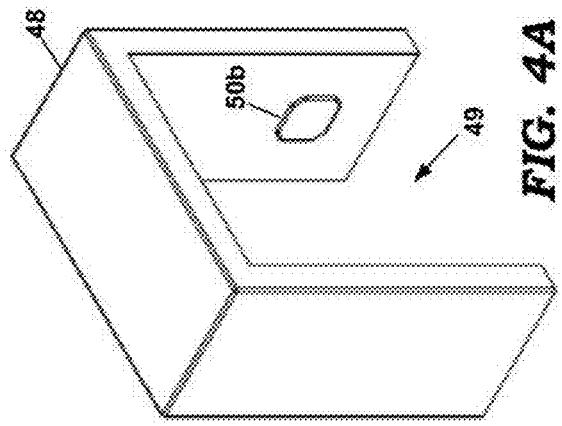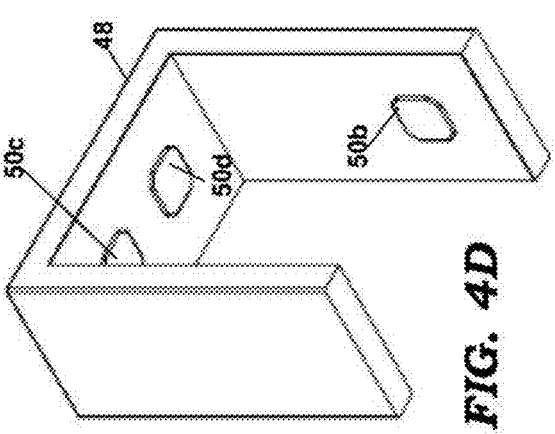

SYSTEM FOR PREVENTION OF FRAUD IN ACCOUNTING FOR UTILIZATION OF MEDICAL ITEMS

RELATED APPLICATIONS

This application claims priority to as a continuation of co-pending U.S. patent application Ser. No. 15/813,208, filed Nov. 15, 2017, titled "System for Prevention of Fraud in Accounting for Utilization of Medical Items," which is a continuation-in-part of U.S. nonprovisional patent application Ser. No. 14/504,859, filed Oct. 2, 2014, titled "System for Sensing and Recording Consumption of Medical Items During Medical Procedure" which granted as U.S. Pat. No. 9,922,304, U.S. nonprovisional patent application Ser. No. 14/587,424, filed Dec. 31, 2014, titled "System for Sensing and Recording Information Regarding Medical Items in a Medical Facility" which granted as U.S. Pat. No. 10,152,688, and U.S. provisional patent application Ser. No. 62/422,295, filed Nov. 15, 2016, titled "System for Prevention of Fraud in Accounting for Utilization of Medical Items," the entire contents of which are incorporated herein by reference.

FIELD

This invention relates to the field of medical item inventory management. More particularly, this invention relates to a system for detecting fraud in the reporting of usage of medial items in the treatment of medical patients.

BACKGROUND

The use of medical supplies and sterile medical devices in the provision of health care services is one of the most significant expenses incurred by most health care facilities. Depending upon the nature and complexity of the medical procedure being performed, a large number of supply items may be used during a medical procedure and, given the priorities of medical personnel involved in the procedure, the ability to track the supplies, gather data about supply utilization and consumption, and record that data in a useable format can be especially difficult. While hospitals and other health care facilities may have sophisticated information systems related to supply inventory management and procedure-based supply requirements, such systems are not able to provide consistent data analysis of supply utilization and optimization if the usage data is not recorded diligently.

If accurate information about the consumption of supplies, devices and instruments during a medical procedure is not captured, then the ability to identify savings opportunities or to accurately bill for all consumed supply items is lost. It is difficult to insure that this logging step is performed accurately and consistently, since the medical personnel are primarily concerned with insuring the success of the medical procedure. Often, the medical personnel do not have time during the procedure to manually log information into a computer for used items that do not include barcodes, or to scan the barcodes of used items that have barcodes. As a result, much of the information winds up being lost during the turnover of the medical procedure room from one case to another. Another problem with inaccurately recording usage information is the possibility of erroneously charging for items that were not used, which can raise regulatory issues.

The Food and Drug Administration (FDA) has established a unique device identification (UDI) system to accurately identify medical devices through the course of their distribution and use. Through implementation of the UDI, the FDA aims to improve patient safety, modernize device post-market surveillance, and facilitate medical device innovation.

A UDI is a unique numeric or alphanumeric code that consists of two parts: a device identifier (DI) and a production identifier (PI). A DI is a mandatory fixed portion of a UDI that identifies the device labeler and the specific version or model of a device. A PI is a conditional, variable portion of a UDI that contains item-specific information, such as the lot or batch number within which a device was manufactured, the serial number and expiration date of a specific device, and the date that a specific device was manufactured. Each UDI is provided in a plain-text version and in a form that uses automatic identification and data capture (AIDC) technology. AIDC technology is any technology that conveys the UDI or the DI of a device in a form that can be entered into an electronic patient record or other computer system via an automated process.

For many products, the PI contains only a lot or batch number. If twenty products having the same DI (e.g. 2.4 mm locking screws or disposable scalpels) are manufactured in the same lot/batch, all twenty products will have the same lot/batch number. If the PI includes only a lot or batch number, it is not possible to differentiate between specific individual devices within the same lot/batch.

As part of the UDI registration process, device labelers must submit certain information about each medical device to the FDA's Global Unique Device Identification Database (GUDID). The current version of the GUDID is comparable to an online phone book. It allows a user to search for a particular DI and download limited device identification information, which may include characteristics of the product, such as whether it contains latex. Currently, registration of a product in the GUDID is a one-time event, and the submitted device information does not include PI information. Following the one-time registration process, dozens of production lots that include potentially millions of products can be manufactured with no update to the GUDID. These millions of medical devices are distributed into the medical care system with no unique device identification that would allow for effective tracking of specific devices.

Currently, Medicare fraud wastes significant amounts of money, resulting in higher health care costs and taxes for everyone. Embodiments of the invention described herein provide for truly unique device identification to facilitate effective device tracking, thereby enabling detection and reduction of Medicare fraud committed by medical providers and suppliers.

SUMMARY

In one aspect, embodiments of the invention use Radio Frequency Identification (RFID) tags to provide the following general functions: (1) identifying medical items or other resources that enter a room or other space in a medical facility; (2) determining where those medical items or other resources came from; and (3) determining whether those medical items or other resources were consumed during a medical procedure performed in the room or space.

In preferred embodiments of the present invention, each item pulled for use during a particular medical procedure in accordance with the Bill of Materials (BOM) for the procedure includes an RFID tag affixed to the item or the item's outer packaging. These RFID tags contain appropriate inventory information regarding each item as maintained in the inventory control system and the Operating Room Information System (ORIS). Each individual item that might be used can be tracked through use of the RFID tags and appropriate RFID reader technology.

In preferred embodiments, each Operating Room (OR) or other procedure room has a shielded enclosure with multiple RFID antennas disposed inside. Preferably, a waste bin or receptacle is disposed in the shielded enclosure. This shielded enclosure and an RFID reader connected to the antennas may be conveniently located near the location where the sterile medical supplies are typically opened by the circulating nurse or other OR personnel responsible for setting up the OR for each procedure, such as near the OR back table. The RFID reader is preferably configured so as to only sense RFID tags that are inside the enclosure and not to sense RFID tags outside the enclosure.

Some preferred embodiments include a portal containing multiple RFID antennas connected to an RFID reader for reading RFID tags on medial items that are passed through the portal. The RFID reader connected to the portal antennas is preferably configured so as to only sense RFID tags that are inside the portal and not to sense RFID tags outside the portal. Preferably, the portal is also conveniently located near the location where the sterile medical supplies are typically opened by the circulating nurse or other personnel responsible for setting up the room for each procedure. The portal may also be located in areas where supplies are stored outside the procedure room and at other transition locations in the medical facility.

Once the packaging of a medical supply is opened, that item is considered "consumed" because the packaging has been compromised and it cannot be re-stocked. In preferred embodiments, as the packaging of medical supply items having RFID tags are opened, the packaging is dropped into the shielded enclosure and the reader reads the RFID tags on that packaging. The RFID reader is connected to a data collection interface, such as an ORIS computer terminal, a tablet computer or smart phone, and the consumption information for each item is logged.

This system provides an accurate way to track supply utilization that does not require additional data input steps from the OR personnel. Simply throwing the discarded packaging into a waste container, which is normal procedure, allows for the RFID tagged supplies to be registered as consumed.

In a further preferred embodiment, a stock bin is provided. Prior to performance of a medical procedure, all RFID-tagged medical supply items that were pulled from the supply room or supply cabinet are placed in the stock bin, the stock bin is moved through the portal or is placed inside the shielded enclosure, and the RFID reader reads the data from the RFID tags on the packaging. In this manner, pre-op data regarding items pulled for use according to a particular BOM can be captured for a given case.

Following the conclusion of the procedure, all RFID-tagged medical supply items that have not been opened, which are thus eligible for re-stocking, are placed into the stock bin, the stock bin is moved through the portal or is placed inside the shielded enclosure, and the RFID reader reads the data from the RFID tags on the packaging. In this manner, post-op data regarding both consumption and non-consumption relative to a given BOM can be captured for a given case. In some embodiments, the RFID reader is connected through a data interface into the ORIS system or the inventory management system and the data regarding the non-consumed items are captured. The process preferably associates medical items (and/or their manufacturer's lot number) and instrument trays to specific patients in the event of a recall or negative occurrence that is determined post-case.

Once the pre-op data and post-op data are accurately collected, the data can be very useful in myriad ways. Since consumption data is accurately determined through the sensing of packaging in the waste bin, billing for medical items consumed in the case can be more accurately reflected on the patient's bill, thereby allowing the hospital to more accurately charge for the procedure. If the stock bin option is included, this ensures that items pulled for the procedure that were detected in the pre-op scan but were not consumed during the procedure are properly returned to inventory. This process also digitally tracks the movement of each item through various transition locations in the medical facility. This makes it possible to identify excessive handling of items and potential exposures to infectious patients.

More sophisticated data analysis can lead to significant cost improvements, such as by trending consumption and non-consumption for multiple procedures and doctors.

In some preferred embodiments, a database is provided (also referred to herein as the UDI Serialized Tracking Database) that complements the FDA's Global Unique Device Identification Database (GUDID). As medical items are produced, manufacturers register the lot and preferably the serial number information for each individual item in the UDI Serialized Tracking Database. More importantly, each individual item registered in the UDI Serialized Tracking Database is assigned a unique identification number encoded in an Electronic Product Code (EPC) in a Radio Frequency Identification (RFID) tag attached to the item. The UDI Serialized Tracking Database maps the unique number to the item's UDI. As each item is consumed during medical treatment and billed to payers, the unique identification number encoded in the EPC of the device is verified and reported. This provides for detection of certain types of fraud in the dispensing of medical items by validating that necessary supplies were actually utilized during patient care (e.g. a wound debridement requires a scalpel, etc.).

One preferred embodiment is directed to an apparatus for recording consumption of medical items used during performance of a medical procedure in a medical facility and for detecting fraud in reporting the consumption of the medial items. The medical items are at least initially enclosed in wrappers having RFID tags disposed in or on the wrappers. A unique identification number that uniquely identifies an individual medical item is encoded in each of the RFID tags. The apparatus preferably includes a shielded enclosure having an internal space for receiving the wrappers of the medical items, RFID antennas disposed within the shielded enclosure, an RFID reader that is electrically connected to the RFID antennas, and a database in which unique identification numbers encoded in RFID tags are cross referenced to Unique Device Identifier (UDI) numbers assigned by a governmental agency to identify specific types of medical items used in medical procedures. A computer is in communication with the database. The shielded enclosure is configured to attenuate radio frequency signals emanated from RFID tags disposed outside the shielded enclosure to levels that are substantially undetectable within the internal space. The RFID antennas receive radio frequency signals emanated from the RFID tags attached to the wrappers disposed within the internal space. The radio frequency signals contain the unique identification numbers encoded in the RFID tags. The RFID reader decodes the unique identification numbers contained in the radio frequency signals emanated from the RFID tags. The computer has a processor that executes instructions for:

(a) receiving the unique identification numbers decoded by the RFID reader, (b) accessing the database to determine whether each of the unique identification numbers decoded by the RFID reader for each medical item is valid for the UDI number assigned to identify the specific type of medical item, (c) accessing the database to determine whether any unique identification number decoded by the RFID reader has been logged into the database as being associated with a medical item that was previously consumed in medical treatment of a patient, and (d) generating a fraud alert message if
any unique identification number decoded by the RFID reader is not valid for the UDI number assigned to identify the specific type of medical item, or
any unique identification number decoded by the RFID reader was previously logged into the database in association with a medical item that previously consumed in medical treatment of a patient.

In some embodiments, the computer is disposed in the medical facility, the computer is in electrical communication with the RFID reader, and the computer executes the instructions for accessing the database and generating a fraud alert message automatically upon receipt of the unique identification numbers decoded by the RFID reader.

In some embodiments, the computer is associated with a medical bill payer entity that receives a bill listing the unique identification numbers decoded by the RFID reader, and the computer executes the instructions for accessing the database and generating a fraud alert message upon entry into the computer of the unique identification numbers listed in the bill.

In another aspect, embodiments are directed to a method for recording consumption of medical items used during performance of a medical procedure and for detecting fraud in reporting the consumption of the medial items. The medical items are at least initially enclosed in wrappers having RFID tags disposed in or on the wrappers. A unique identification number that uniquely identifies an individual medical item is encoded in each of the RFID tags. A preferred embodiment of the method includes the following steps:

(a) storing a plurality of unique identification numbers in a database in association with Unique Device Identifier (UDI) numbers assigned by a governmental agency to identify specific types of medical items used in medical procedures;

(b) during the performance of the medical procedure, depositing the wrappers of the medical items into an internal space of a shielded enclosure that is configured to attenuate radio frequency signals emanated from RFID tags disposed outside the shielded enclosure to levels that are substantially undetectable within the internal space;

(c) receiving radio frequency signals emanated from RFID tags attached to or embedded in the wrappers disposed within the internal space, wherein the radio frequency signals contain the unique identification numbers encoded in the RFID tags;

(d) decoding the unique identification numbers contained in the radio frequency signals emanated from the RFID tags;

(e) accessing the database to determine whether each of the unique identification numbers decoded from the radio frequency signals is valid for the UDI number assigned to identify the specific type of medical item;

(f) accessing the database to determine whether any of the unique identification numbers decoded from the radio frequency signals was previously logged into the database as being associated with a medical item that was previously consumed during medical treatment of a patient, and (g) generating a fraud alert message if
any unique identification number decoded from the radio frequency signals is not valid for the UDI number assigned to identify the specific type of medical item, or
any unique identification number decoded from the radio frequency signals was previously logged into the database in association with a medical item that was previously consumed in medical treatment of a patient.

In some embodiments, steps (e), (f) and (g) are performed by a computer that is disposed in the medical facility and is in electrical communication with the RFID reader. In these embodiments, steps (e), (f) and (g) are performed automatically upon completion of step (d).

In some embodiments, steps (e), (f) and (g) of the method are performed by a computer that is associated with a medical bill payer entity that receives a bill listing the unique identification numbers decoded by the RFID reader. In these embodiments, steps (e), (f) and (g) are performed upon entry into the computer of the unique identification numbers listed in the bill.

BRIEF DESCRIPTION OF THE DRAWINGS

Other embodiments of the invention will become apparent by reference to the detailed description in conjunction with the figures, wherein elements are not to scale so as to more clearly show the details, wherein like reference numbers indicate like elements throughout the several views, and wherein:

FIGS. 4A-4F depict a portal according to an embodiment of the invention;

DETAILED DESCRIPTION

Figure 1:
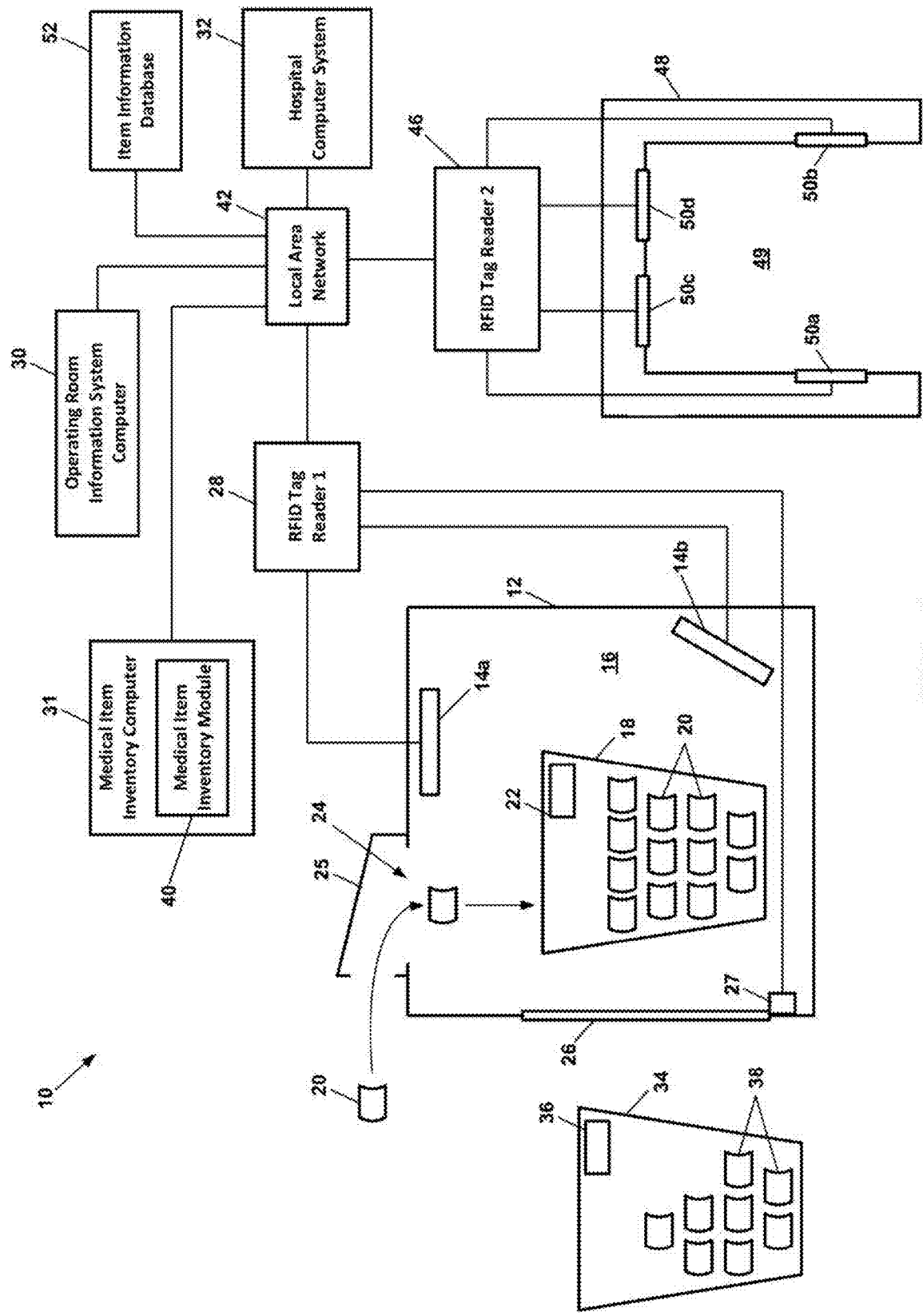
FIG. 1 depicts a system for sensing and recording consumption of medical items during a medical procedure according to an embodiment of the invention.

As the term is used herein, a "medical item" is an item, material, substance, or piece of durable medical equipment (DME) that is used or consumed during the performance of a medical procedure or that is dispensed to a patient to treat a medical condition or provide comfort to the patient. For example, sponges, gloves and drapes are medical items. A surgical implant is another example of a medical item. Knee braces, negative pressure wound therapy units, blood glucose monitors, and wheelchairs are further examples of medical items. Medical items comprise a subset of "medical resources." As the term is used herein, a "medical resource" is any item, person, piece of equipment, or space involved in providing medical services for a patient. For example, a gurney on which a patient lies during a surgical procedure is a medical resource. The doctor performing the procedure, the attending nurses, and the patient are also medical resources. An operating room is a medical resource.

As the term is used herein, a "wrapper" encompasses all manner of containers and packaging, sterile or non-sterile, in which a medical item is or has been enclosed. The term "wrapper" also includes a label, hang tag, or other such device that may be attached to a medical item without completely enclosing the item. The term "wrapper" further includes packaging for a sterile-wrapped kit of medical items, such as a tray of implants and supplies for use in a surgical procedure, wherein an RFID tag is attached to the tray. Generally, anything that may function to associate an RFID tag with a medical item is encompassed by the term "wrapper."

Each medical item has a unique item identifier encoded in a machine-readable code in an RFID tag, a QR code, a bar code, or a combination thereof attached to the medical item or its wrapper. In some embodiments, an RFID tag and a QR code are combined in a single label applied to the medical item or its wrapper.

In a preferred embodiment, each wrapper includes an RFID tag attached thereto or embedded therein. Ultra-High Frequency (UHF) passive RFID tags are preferred for this application, as they may be interrogated from up to about 30 centimeters away. In preferred embodiments, each RFID tag is encoded with a unique item identification number for the particular medical item associated with the wrapper. An item information database 52 associates each item identification number with item-specific information, such as the manufacturer part number, item description, vendor, cost, Latex content, expiration date, and inventory location. Additionally or alternatively, the RFID tag may be encoded with item-specific information as set forth in Unique Device Identification (UDI) standards set by the U.S. Food and Drug Administration (FDA).

In some embodiments, item-specific information encoded in RFID tags on medical items may be used to generate alerts for medical personnel. For example, an alert may be generated if information encoded in an RFID tag indicates the presence of Latex in an item, and the patient is allergic to Latex. Also, an alert may be generated if information encoded in an RFID tag indicates that an item's useful lifetime has expired or if the item is from a lot that has been recalled by the manufacturer.

As the term is used herein, a "portal" is any passageway, opening, aperture, window, panel, wall, doorway, hallway, pathway, or aisle in or near which one or more RFID antennas are mounted for sensing RFID tags that pass through or near the portal. A portal may also be a handheld scanning device for reading RFID tags. Several portals may be used to track the routes of travel and locations of medical resources throughout a medical facility or a medical item supplier facility.

As the term is used herein, a "scan" for RFID tags refers to operations performed by an RFID reader to transmit signals and receive signals from RFID tags that are in range of the RFID reader and its associated antenna(s).

In preferred embodiments, portals are placed at "transition locations" within a medical facility or a medical item supplier facility. Examples of transition locations include supply rooms, supply cabinets, procedure rooms, waste containers, personnel break rooms, hallways, shipment assembly areas, shipment loading docks, and points of entry into and exit from the medical facility or a medical item supplier facility.

As the term is used herein, a "shipment" of medical items comprises multiple medical items, of the same type or different types, that are packaged together at a supplier location and shipped to a location at which the medical items are consumed or dispensed. Generally, each shipment includes a packing list that lists all of the medical items in the shipment. In preferred embodiments, each packing list has a unique shipment identifier that encodes shipment identification information that is specific to the shipment. The shipment identifier may be in the form of an RFID tag, bar code, or other encoded identifier attached to, embedded in, or printed on the packing list.

Sensing and Logging Consumption of Medical Items During Medical Procedure

As shown in FIG. 1, a system 10 for sensing and logging consumption of medical items during a medical procedure includes a shielded enclosure 12 having a space 16 that is preferably large enough to receive a waste bin 18. Disposed within the enclosure 12 are two RFID antennas 14a and 14b, such as Laird 5×5 inch Mini Far Field antennas (model number S9025PLNF) having left-hand circular polarization and operating in the 902-928 MHz frequency range. One of the antennas 14a is preferably disposed at the top of the enclosure 12, with its field of view looking downward into the space 16. The other RFID antenna 14b is preferably disposed at the bottom of the enclosure 12, with its field of view looking upward into the space 16. The RFID antennas 14a-14b are electrically connected, such as via a coaxial cable, to a UHF RFID tag reader 28. In a preferred embodiment, the RFID tag reader 28 is an Impinj® Speedway® model R420.

Figure 2B:
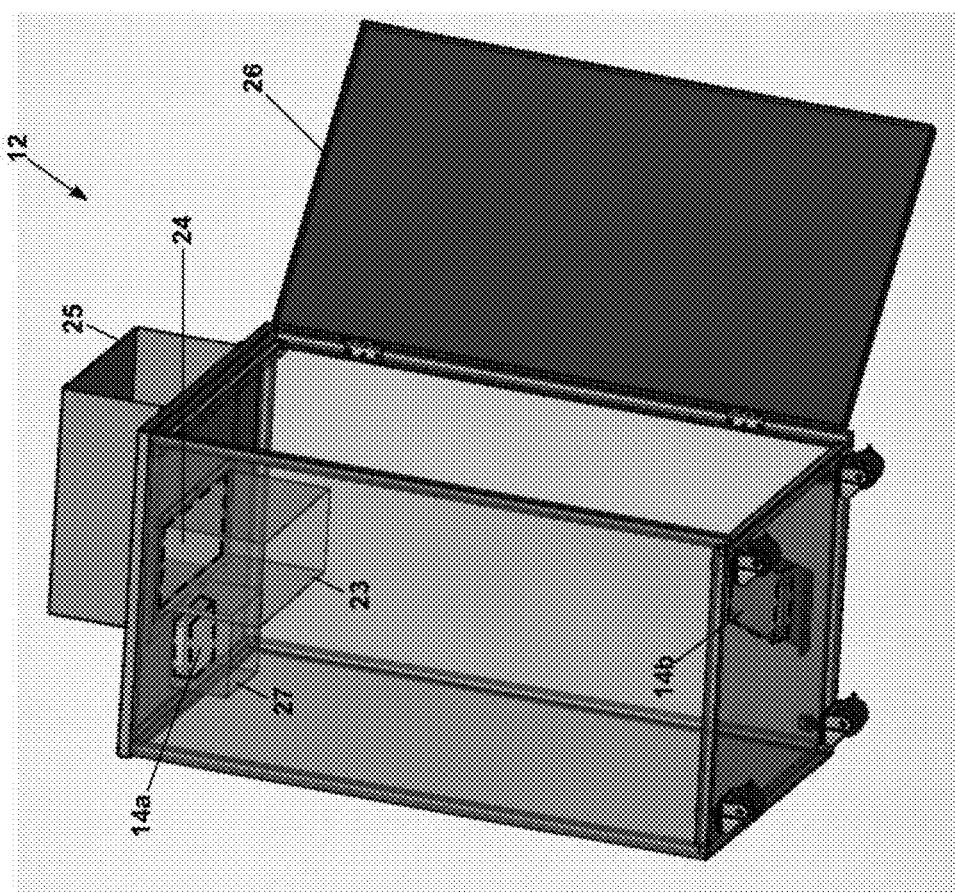
FIGS. 2A and 2B depict shielded enclosures according to embodiments of the invention.
Figure 2A:
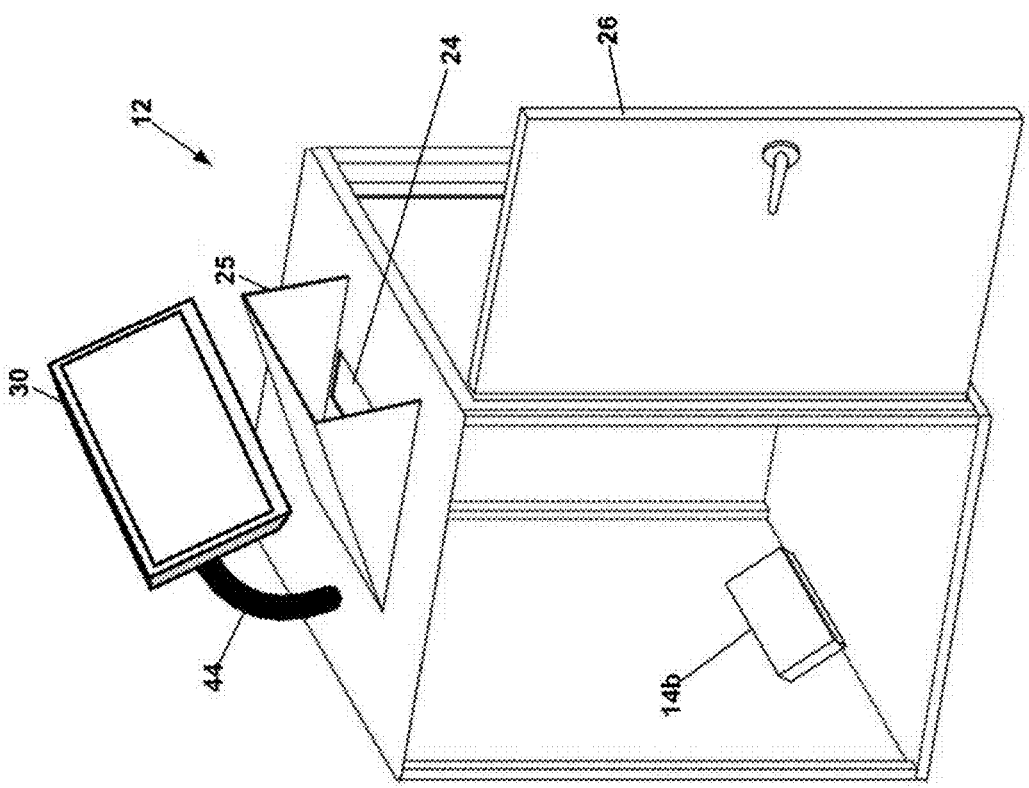

Preferred embodiments of the shielded enclosure 12 are shown in FIGS. 2A and 2B, wherein the sidewalls are depicted as transparent. The enclosure 12 is preferably made from 0.080 inch thick sheet aluminum supported by 0.75× 0.75 inch square aluminum tubing (0.125 thick). The outside dimensions of the preferred embodiment are 23.5×22.0× 40.75 inches.

As the term is used herein, "shielded" means that the enclosure 12 is designed to prevent the antennas 14a-14b from receiving RFID signals from RFID tags located outside the enclosure 12 at a signal-to-noise ratio high enough to trigger detection of those outside RFID tags. For purposes of this disclosure, "shielded" does not mean that absolutely all RF energy is blocked from entering the enclosure, as this would require unnecessary levels of shielding.

In some embodiments, an opening 24 is provided in the top of the enclosure that is large enough to receive wrappers or containers 20 from which medical items have been removed. The opening 24 is preferably a 6.75×13.75 inch rectangle. An aluminum cover 25 is provided over the opening 24. The cover may be slanted as shown in FIG. 2A or more box-like as shown in FIG. 2B to prevent signals from escaping the enclosure 12. As shown in FIG. 2B, the enclosure preferably includes an aluminum chute 23 around the opening 24, and an aluminum shield 27 around the antenna 14a. These structures provide further attenuation of RFID signals originating outside the enclosure 12 to prevent those signals from being detected by the antennas 14a-14b. The waste bin 18 is positioned below the opening 24 so that wrappers 20 deposited in the opening 24 fall into the bin 18. In a preferred embodiment, a hinged door 26 large enough to receive the waste bin 18 is provided in a sidewall of the enclosure 12. The door 26 is preferably 29.5×39.25 inch, and includes a handle/latch for securing the door in a closed position. The enclosure 12 is considered to be shielded when the door 26 is closed.

In a preferred embodiment, the system 10 includes a portal 48 having an opening 49 at least large enough to receive the waste bin 18. The portal 48 is preferably equipped with four RFID antennas 50a-50d having fields of view looking inward into the portal opening 49. The RFID antennas 50a-50d are electrically connected, such as via coaxial cables, to a UHF RFID tag reader 46. In a preferred embodiment, the RFID tag reader 46 is an Impinj® Speedway® model R220. In some embodiments, the tag reader 46 and the tag reader 28 comprise a single tag reader.

The waste bin 18, also referred to herein as a waste tote, is preferably a plastic container having an open top for receiving wrappers 20. In some embodiments, an RFID tag 22 encoded with a unique bin identification number is attached to the waste bin 18. The database 52 associates the bin identification number with a particular procedure room to which the waste bin 18 is assigned. Alternatively, the RFID tag 22 may be encoded with information indicating the procedure room to which the bin 18 is assigned.

The RFID tag readers 28 and 46 are electrically connected via a local area network (LAN) 42 to a medical item inventory computer 31, which may be a server computer, desktop computer, laptop computer, tablet computer or other mobile computing device. Alternatively, the electrical connection between the RFID tag readers 28 and 46 and the computer 31 is via a Universal Serial Bus (USB) interface. The computer 31 includes memory for storing and a processor for executing instructions of a medical item inventory module 40. In preferred embodiments, the medical item inventory module 40 compiles pre-op and post-op lists of items, compares the lists to detect discrepancies, generates alert messages upon detection of discrepancies, and updates inventory records based on actual item usage.

In a preferred embodiment, an Operating Room Information System (ORIS) computer 30 is in communication with the medical item inventory computer 31 via a communication network, such as the LAN 42. The ORIS computer 30 is also in communication with a hospital computer system 32 via a communication network, such as the LAN 42. In preferred embodiments, the hospital computer system 32 manages medical item inventories, operating room scheduling, patient records, insurance reimbursement/payment functions, and admission/discharge/transfer (ADT) records. The hospital computer system 32 may also include or be connected to an electronic data interchange server, such as a J.D. Edwards/Oracle server, that implements electronic commerce transactions between the hospital and medical item suppliers.

In some embodiments, the medical item inventory module 40 is a software application running on the computer 31. In alternative embodiments, the medical item inventory module 40 is executed by a remote computer (outside the OR). For example, the medical item inventory module 40 may be implemented as "software-as-a-service" provided via the Internet by a medical item inventory service provider.

With continued reference to FIG. 1, a preferred embodiment of the system 10 includes a stock bin 34, which may also be referred to herein as a transport bin or stock tote. As described in more detail below, the stock bin 34 is used to transfer medical items 38 to be used during a medical procedure from a stock room to the procedure room, and to transfer unused medical items 38 from the procedure room back to the stock room. In some embodiments, an RFID tag 36 is attached to the stock bin 34 that is encoded with a unique bin identification number. In some embodiments, the database 52 associates the bin identification number with a particular procedure room or stock room to which the stock bin 34 is assigned. Alternatively, the RFID tag 36 may be encoded with information indicating the procedure room or stock room to which the stock bin 34 is assigned.

Figure 3:
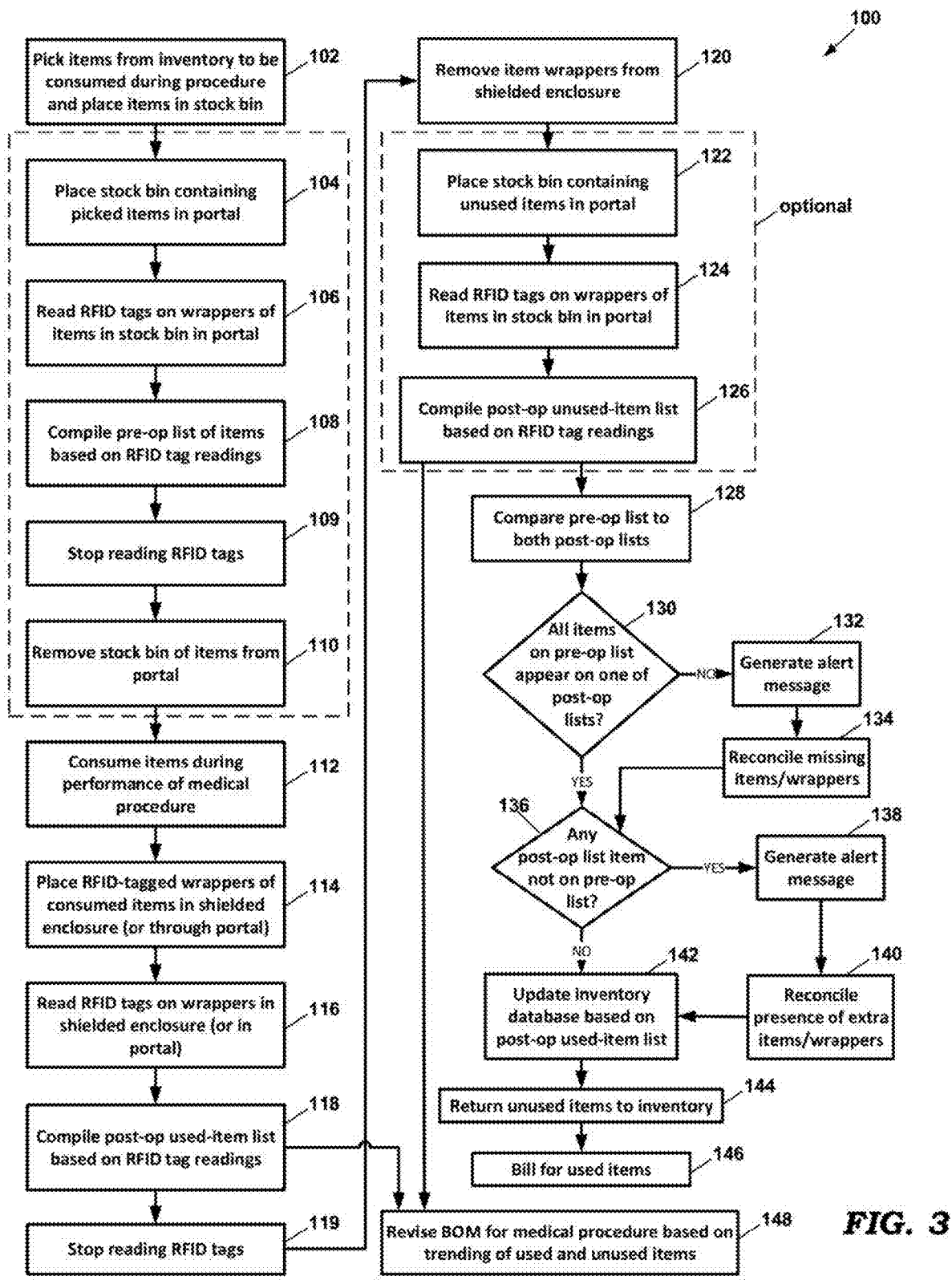
FIG. 3 depicts a method for sensing and recording consumption of medical items during a medical procedure according to an embodiment of the invention.

FIG. 3 depicts a preferred embodiment of a process 100 for sensing and recording consumption of medical items during a medical procedure using the system depicted in FIG. 1. To begin the process, hospital personnel pick medical items from inventory stock to be used during the medical procedure (step 102 in FIG. 3). For example, the needed items may be listed on a Bill of Materials (BOM) for the particular type of procedure to be performed. In some cases, the BOM also reflects the individual preferences of particular doctors. These types of BOM's may also be referred to as Doctor Preference Cards. The picked items are placed in the stock bin 34 to be transferred to the OR.

In one embodiment, the stock bin 34 containing the picked items 38 is placed in or passed through the portal 48 outside the procedure room (step 104) and the RFID reader 46 reads the RFID tags on the wrappers of the items 38 in the stock bin 34 (step 106). In some embodiments, activation of the reader 28 is triggered manually by a person in the procedure room using an interface device (mouse, touchpad or keyboard) of the computer 31.

The item identification numbers read from the RFID tags in the portal 48 are transferred to the medical item inventory computer 31 where the medical item inventory module 40 compiles a pre-op list of the items 38 in the stock bin 34 (step 108). In a preferred embodiment, the date/time of the compilation of the list is recorded in the medical item inventory computer 31, along with the identification number of the stock bin 34. Other information may be associated with the pre-op list, such as procedure room number, doctor name, patient name, patient age, patient weight, patient allergies, type of medical procedure, and case number. Once the pre-op list is compiled, the RFID reader 28 may be deactivated (step 109) and the stock bin 34 removed from the portal 48 (step 110).

Steps 104-110 of FIG. 3 are optional and are not implemented in all embodiments of process 100. If these steps are not performed, the BOM for the medical procedure may serve the purpose of the pre-op item list.

The items 38 are preferably removed from the bin 34 and arranged on a table in the procedure room according to the doctor's or attending nurse's preference. As the items 38 are used/consumed during the procedure (step 112), wrappers 20 removed from the items 38 are dropped through the opening 24 in the enclosure 12 where they are received into the waste bin 18 (step 114). When the wrappers 20 enter the enclosure 12, the RFID tags on the wrappers 20 are detected and read by the reader 28 (step 116). It will be appreciated that a waste bin 18 is not absolutely necessary for this process. However, the use of a waste bin 18 makes collection and removal of the wrappers 20 easier.

The item identification numbers read from the RFID tags in the enclosure 12 are transferred to the medical item inventory computer 31 where the medical item inventory module 40 compiles a post-op used-item list of the wrappers 20 (step 118). In a preferred embodiment, the date/time that each wrapper 20 was first detected is recorded in the list. Also, the identification number of the waste bin 18 (if any) and other information may be associated with the post-op used-item list, such as procedure room number, doctor name, patient name, type of medical procedure, and case number. Once the post-op used-item list is compiled, the RFID reader 28 is deactivated (step 119) so that it will not read any other tags when the door 26 is opened to remove the wrappers 20 (step 120). Deactivation of the reader 28 may be triggered by opening the door 26 of the enclosure 12.

In an alternative embodiment, the waste bin 18 remains outside the shielded enclosure 12 during the procedure. As the items 38 are used/consumed during the procedure (step 112), wrappers 20 removed from the items 38 are deposited in the waste bin 18. After completion of the procedure, the waste bin 18 containing the wrappers 20 is placed through the portal 48 (step 114), and the reader 28 reads the RFID tags of the wrappers 20 (step 116). The post-op used-item list is compiled as described in the previous embodiment (step 118).

In some embodiments, after completion of the medical procedure, all unused items 38 are placed back into the stock bin 34, and the stock bin 34 is passed through the portal 48 (step 122). The reader 46 reads the RFID tags of the unused items 38 (step 124), and a post-op unused-item list is compiled (step 126). The identification number of the stock bin 34 and other information may be associated with the post-op unused-item list, such as procedure room number, doctor name, patient name, type of medical procedure, and case number.

Steps 122-126 of FIG. 3 are optional and are not implemented in all embodiments of process 100. If these steps are not performed, the post-op unused-item list may be generated by comparing the BOM to the post-op used item list.

Various embodiments of the invention use the pre-op and post-op item lists to implement various advantageous inventory and billing functions. For example, the medical item inventory module 40 may compare the items listed in the pre-op list to the items listed in the post-op used-item list and the post-op unused-item list (step 128). If an item in the pre-op list does not appear on either of the post-op lists (step 130), this means the item was brought into the procedure room but neither the item nor its wrapper ended up in the stock bin or the waste bin after the procedure. In this case, an alert is generated that causes a message to appear on a display screen of the ORIS computer 30 or the medical item inventory computer 31 (step 132). The alert should prompt the procedure room personnel to investigate three possibilities that may have caused the discrepancy: (1) the item is unused and still in the procedure room but was inadvertently not placed back into the stock bin before the post-op unused-item list was compiled, (2) the item was used and its wrapper is still in the procedure room but the wrapper was inadvertently not placed in the waste bin before the post-op used-item list was compiled, or (3) the item and/or its empty wrapper was removed from the procedure room prior to compilation of either of the post-op lists. In any event, the missing item(s) or wrapper(s) should be located and the pre-op and post-op lists reconciled (step 134).

If the comparison of the pre-op and post-op item lists indicates that an item that appears on either of the post-op lists is not on the pre-op list (step 136), this means that the item or its wrapper was present in the procedure room when the post-op lists were compiled, but it was (1) not brought into the procedure room in the stock bin with the other items, or (2) brought into the procedure room in the stock bin but was removed from the stock bin prior to compilation of the pre-op list. In this case, an alert is generated which causes a message to appear on a display screen of the computer 31 (step 138). The alert should prompt the procedure room personnel to investigate what may have caused the discrepancy and reconcile the pre-op and post-op lists (step 140).

In a preferred embodiment, once the post-op lists are complete and reconciled, the computer 31, the ORIS computer 30, or the hospital computer system 32 uses the lists to update the database 52 based on actual item usage (step 142). The hospital computer system 32 or the ORIS computer 30 also may use the post-op used-item list to accurately bill the patient (or insurance company) for the items used during the procedure (step 146). The stock bin 34 may be returned to the appropriate inventory stock room where the unused items 38 may be returned to inventory (step 144).

In preferred embodiments, the hospital computer system 32 or the Medical Item Inventory Application 40 analyzes the post-op unused-item lists generated during multiple procedures of the same type and for the same doctor to determine trends in the lack of usage of certain medical items that are listed on BOM's (step 146). This trend data may be used to revise the BOM's for certain procedures/doctors. For example, if the trend data indicates that in 90% of hip replacement surgeries performed by Dr. Jones only three sponges of a particular type are used out of the five called for on the BOM, the BOM may be revised to call for only three sponges. Revisions of this sort would reduce the effort/cost associated with returning unused items to the stock room, and would decrease traffic in and out of the procedure room during a procedure which would decrease the chances of a site infection. Trend data may also be used to determine the optimal locations to store medical supplies and the optimal quantities to store.

Tracking Utilization of Medical Resources in Medical Facility

Figure 5:
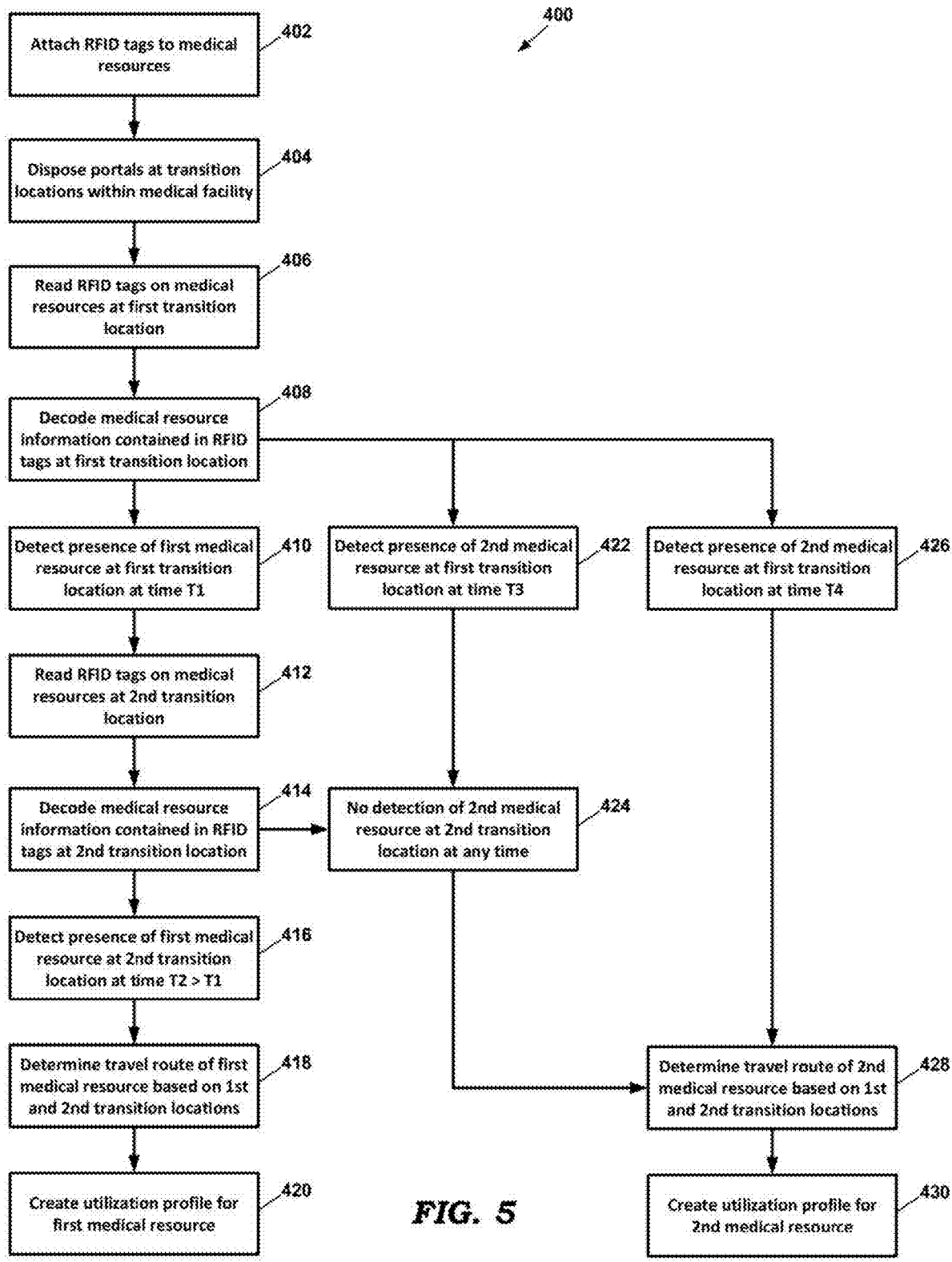
FIGS. 5 and 6 depict processes for sensing and recording utilization of medical resources in the performance of a medical procedure in a medical facility according to embodiments of the invention.

Various embodiments described herein provide systems for sensing RFID tags attached to various medical resources at various transition locations throughout a medical facility, for tracking routes of movement of the medical resources based on the sensing of the RFID tags, for detecting relationships between medical resources based on sensing their RFID tags at the same transition locations during overlapping time periods, for analyzing utilization of the medical resources, and for developing utilization profiles. For example, FIG. 5 depicts an embodiment of a process 400 for analyzing the utilization of two different medical resources based on sensing (or not sensing) their RFID tags at two different transition locations within a medical facility. The process 400 involves attaching RFID tags to medical resources (step 402), disposing RFID-sensing portals at various transition locations within the medical facility (step 404), reading medical resource information from the RFID tags using the portals (step 406 and 412), and decoding the medical resource information to identify the medical resources (step 408 and 414) and determine various characteristics of the resources as described in more detail below.

For example, with continued reference to FIG. 5, a first medical resource is detected at a first transition location at a time T1 (step 410) and at a second transition location at a time T2 (step 416). Based on these detections, the system determines that the first medical resource travelled from the first transition location to the second transition location between times T1 and T2 (step 418). Based on this route of travel and the times of detection, the system creates a utilization profile for the first medical resource (step 420).

A second medical resource is detected at the first transition location at a time T3 (step 422), which may be less than, greater than, or equal to time T1. The second medical resource is again detected at the first transition location at a time T4 (step 426), which is occurs after time T3 (T4>T3). There is no detection of the second medical resource at the second transition location between times T3 and T4 (step 424). Based on these detections, the system determines that the second medical resource travelled from the first transition location back to the first transition location between times T3 and T4, and did not travel to the second transition location (step 428). Based on this route of travel and the times of detection, the system creates a utilization profile for the second medical resource (step 430).

In the example of FIG. 5, the first transition location may be an entrance/exit door of a medical procedure room PR1 within a medical facility, the second transition location may be a waste container WC1 within the medical procedure room PR1, the first medical resource may be a first medical item that was picked to be used during a medical procedure MP1 in the procedure room PR1, and the second medical resource may be a second medical item that was picked to be used during the same medical procedure MP1 in the procedure room PR1. Based on the detections described above, the system determines that the first medical item entered the medical procedure room PR1 (first transition location) at time T1, and it or its wrapper was deposited in the waste container WC1 (second transition location) at time T2. Based on this route of travel, the system creates a utilization profile indicating that the first medical item was used or consumed during the medical procedure MP1. Also based on the detections described above, the system determines that the second medical item entered the medical procedure room PR1 (first transition location) at time T3, exited the medical procedure room PR1 (first transition location) at time T4, and was not deposited in the waste container WC1 (second transition location). Based on this route of travel, the system creates a utilization profile indicating that the second medical item was brought into the medical procedure room PR1, but was not used during the medical procedure MP1.

Figure 6:
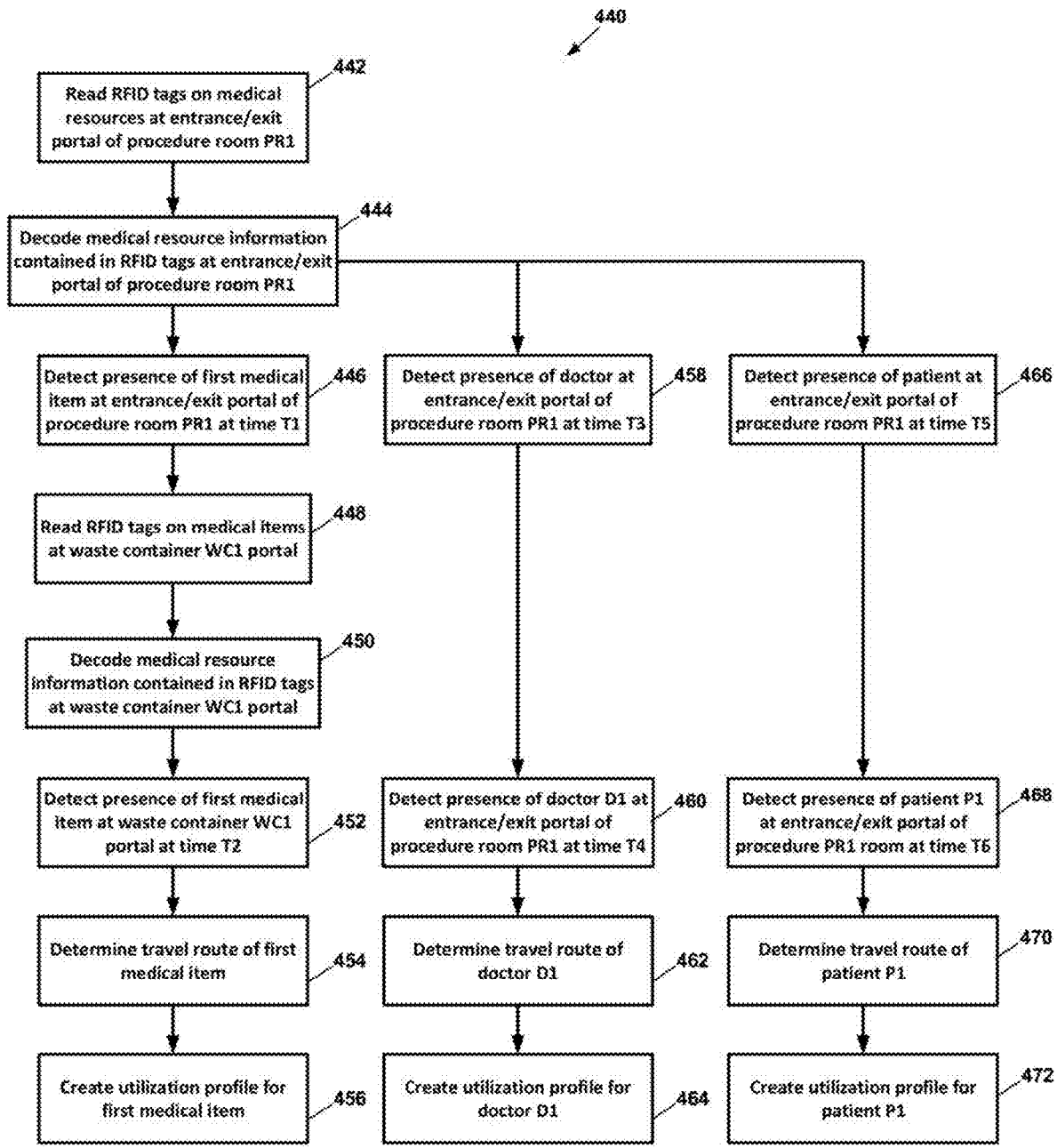

FIG. 6 depicts an embodiment of a process 440 for analyzing the utilization of three different medical resources based on their RFID tags being sensed (or not sensed) at two different transition locations within a medical facility. The process 440 involves reading medical resource information from RFID tags attached to three medical resources—a first medical item, a doctor, and a patient—using portals at the entrance/exit of a procedure room PR1 and on a waste container WC1 (step 442 and 448), and decoding the medical resource information to identify the medical resources (step 444 and 450) and determine various characteristics of the resources. As in the previous example, the system determines that the first medical item entered the medical procedure room PR1 at time T1, and it or its wrapper was deposited in the waste container WC1 at time T2 (step 454). Based on this route of travel, the system creates a utilization profile indicating that the first medical item was used during the medical procedure MP1 (step 456).

With continued reference to FIG. 6, the system detects the doctor D1 entering the medical procedure room PR1 at time T3 which may be less than, greater than, or equal to time T1 (step 458). The doctor D1 is detected leaving the medical procedure room PR1 at time T4 which is greater than T1 and T3 (step 460). Based on this route of travel, the system creates a utilization profile indicating that the doctor D1 was involved in a medical procedure MP1 in the procedure room PR1 between times T3 and T4 (step 464). In preferred embodiments, the utilization profile for the doctor D1 indicates that the first medical item was consumed or used during a medical procedure MP1 performed by the doctor D1. In some embodiments, the utilization profile for the first medical item also indicates that the first medical item was consumed or used during a medical procedure MP1 performed by the particular doctor D1.

With continued reference to FIG. 6, the system detects the patient P1 entering the medical procedure room PR1 at time T5 which may be less than, greater than, or equal to time T1 (step 466). The patient P1 is detected leaving the medical procedure room PR1 at time T6 that is greater than T1 and T5 (step 468). Based on this route of travel, the system creates a utilization profile indicating that the patient P1 was involved in a medical procedure MP1 in the procedure room PR1 between times T5 and T6 (step 470). In preferred embodiments, the utilization profile for the patient P1 also indicates that the first medical item was consumed or used during the medical procedure MP1 performed on the patient P1 by the particular doctor D1. In some embodiments, the utilization profile for the first medical item also indicates that the first medical item was consumed or used during the medical procedure MP1 performed on the particular patient P1. In some embodiments, the utilization profile for the doctor D1 also indicates that the first medical item was consumed or used during the medical procedure MP1 performed on the particular patient P1.

Generating Alerts Based on Utilization of Medical Resources in Medical Facility

Figure 7:
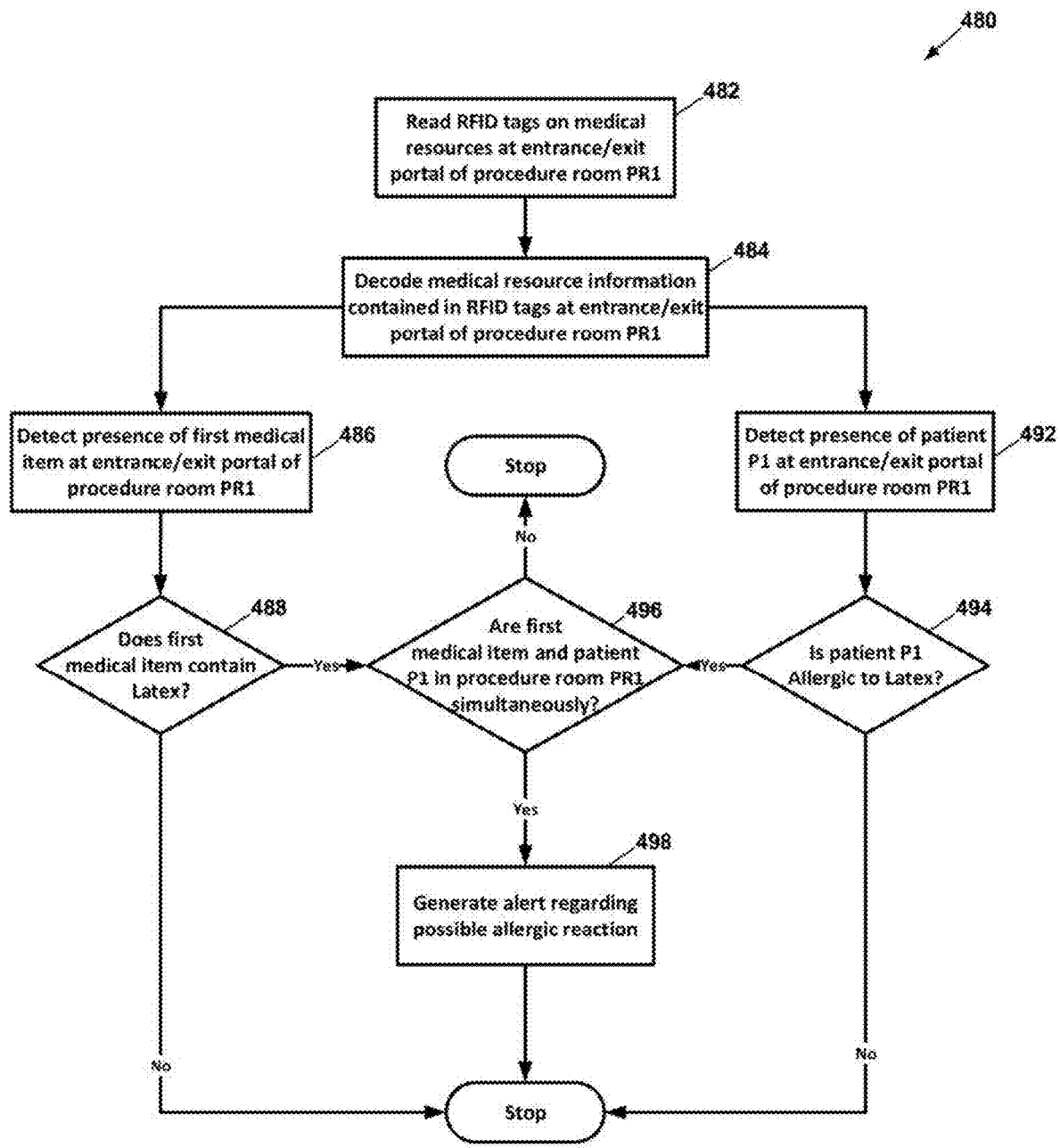
FIGS. 7 and 8 depict processes for generating alerts based on utilization of medical resources in the performance of a medical procedure in a medical facility according to embodiments of the invention.

FIG. 7 depicts a preferred embodiment of a process 480 for generating an alert based on utilization of medical resources in the performance of a medical procedure in a medical facility. This process 480 analyzes the utilization of two different medical resources based on sensing their RFID tags at the same transition location within the medical facility. The process 480 involves reading medical resource information from RFID tags attached to the two medical resources—a first medical item and a patient P1—using portals at the entrance/exit of a procedure room PR1 (step 482), and decoding the medical resource information to identify the medical resources (step 484) and to determine various characteristics of the resources. For example, the medical resource information decoded at step 484 may indicate whether the first medical item contains a potential allergenic, such as Latex, and whether the patient P1 is allergic to any drugs or substances, such as Latex. Using the decoded information, the system detects that the first medical item entered the medical procedure room PR1 (step 486) at a certain time and that the patient P1 entered the medical procedure room PR1 at a certain time (step 492). If the first medical item contains a substance to which the patient P1 is allergic, and the first medical item and the patient P1 are in the procedure room PR1 simultaneously (steps 488, 494 and 496), the system generates an alert informing personnel in the procedure room PR1 of the potential for a harmful allergic reaction (step 498). This alert may be audible (siren) and visible (strobe lights) in the procedure room, and it may be sent via electronic messaging to other personnel within the medical facility to give notice of the situation. In preferred embodiments, the occurrence of such an event is also reflected in the utilization profile of the patient P1.

In some embodiments, the system generates a potential allergic reaction alert if an RFID reader portal at the doorway of a supply room detects a medical item leaving the supply room that was picked for use during a medical procedure involving a patient that is allergic to a substance in the medical item. This detection could also be made by any RFID reader portal at any transition location between the supply room and the medical procedure room.

Figure 8:
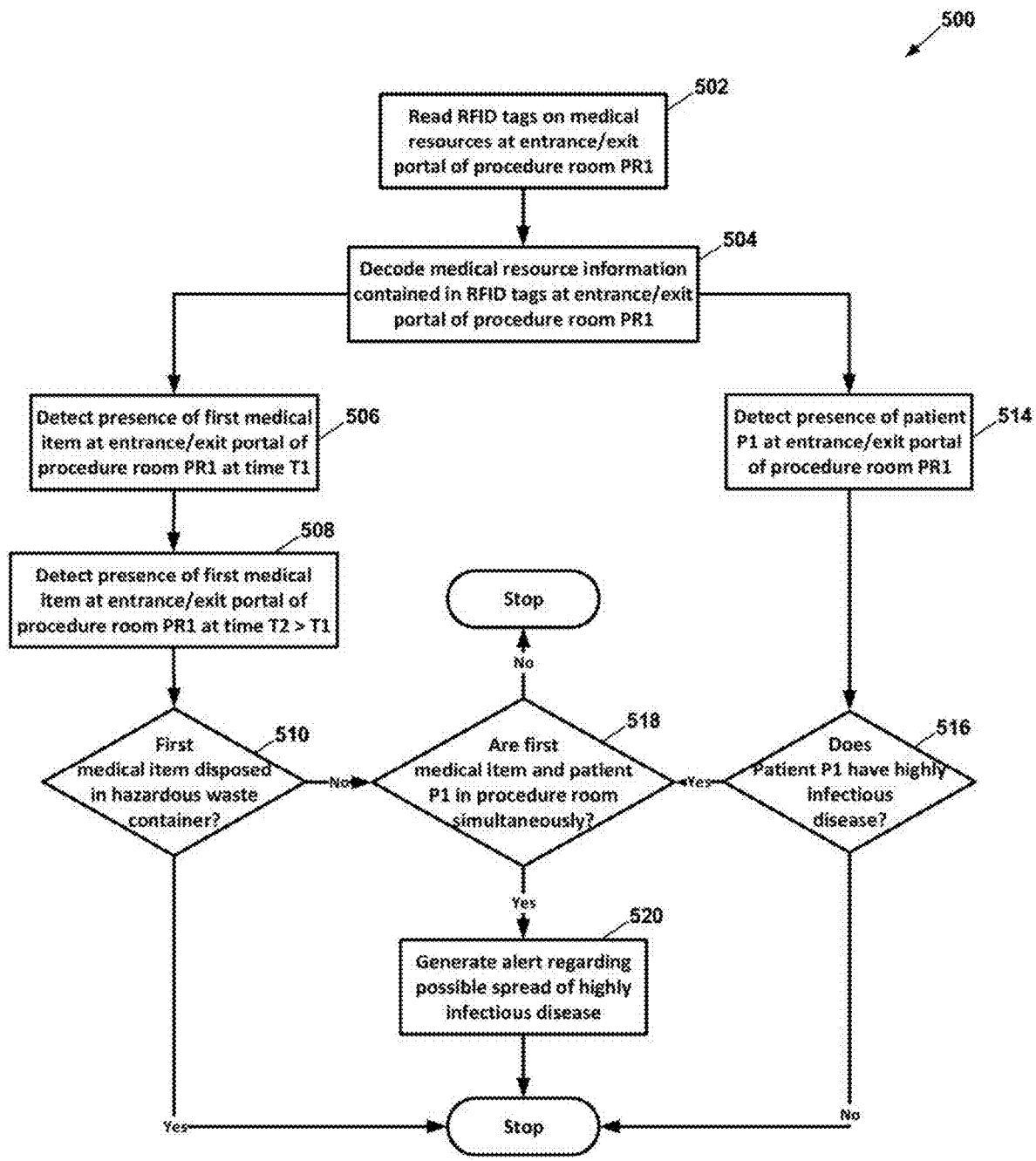

FIG. 8 depicts a preferred embodiment of another process 500 for generating an alert based on utilization of medical resources in the performance of a medical procedure in a medical facility. This process 500 analyzes the utilization of two different medical resources based on sensing their RFID tags at the same transition location within the medical facility. The process 500 involves reading medical resource information from RFID tags attached to the two medical resources—a first medical item and a patient P1—using portals at the entrance/exit of a procedure room PR1 (step 502), and decoding the medical resource information to identify the medical resources (step 504) and to determine various characteristics of the resources. For example, the medical resource information decoded at step 504 may indicate that the patient P1 is infected with a highly infectious contagion, such as Methicillin-resistant *Staphylococcus aureus* (MRSA). Using the decoded information, the system detects that the first medical item entered the medical procedure room PR1 (step 506) at time T1 and that the patient P1 entered the medical procedure room PR1 at a certain time (step 514). The system later detects that the first medical item has exited the medical procedure room PR1 (step 508) at time T2. If the first medical item was not deposited in a hazardous waste container prior to leaving the procedure room PR1, and the first medical item and the patient P1 were in the procedure room PR1 simultaneously, and the patient P1 is infected with a contagion such as MRSA (steps 510, 516, 518), the system generates an alert informing personnel in the procedure room PR1 of a potential for spread of a highly infectious contagion due to possible contact with the first medical item (step 520). This alert may be audible (siren) and visible (strobe lights) in the procedure room, and it may be sent via electronic messaging to other personnel within the medical facility to give notice of the situation. In preferred embodiments, the occurrence of such an event is also reflected in the utilization profile of the first medical item. In some situations, the determination that the patient is infected (step 516) may be made after the procedure is complete and the patient has left the procedure room. In such situations, the system will generate the alert (step 520) after information indicating the patient's infection is entered into the patient's record (the medical resource information for the patient.)

Tracking Custody of Medical Items in Supply and Consumption Chain

Figure 9:
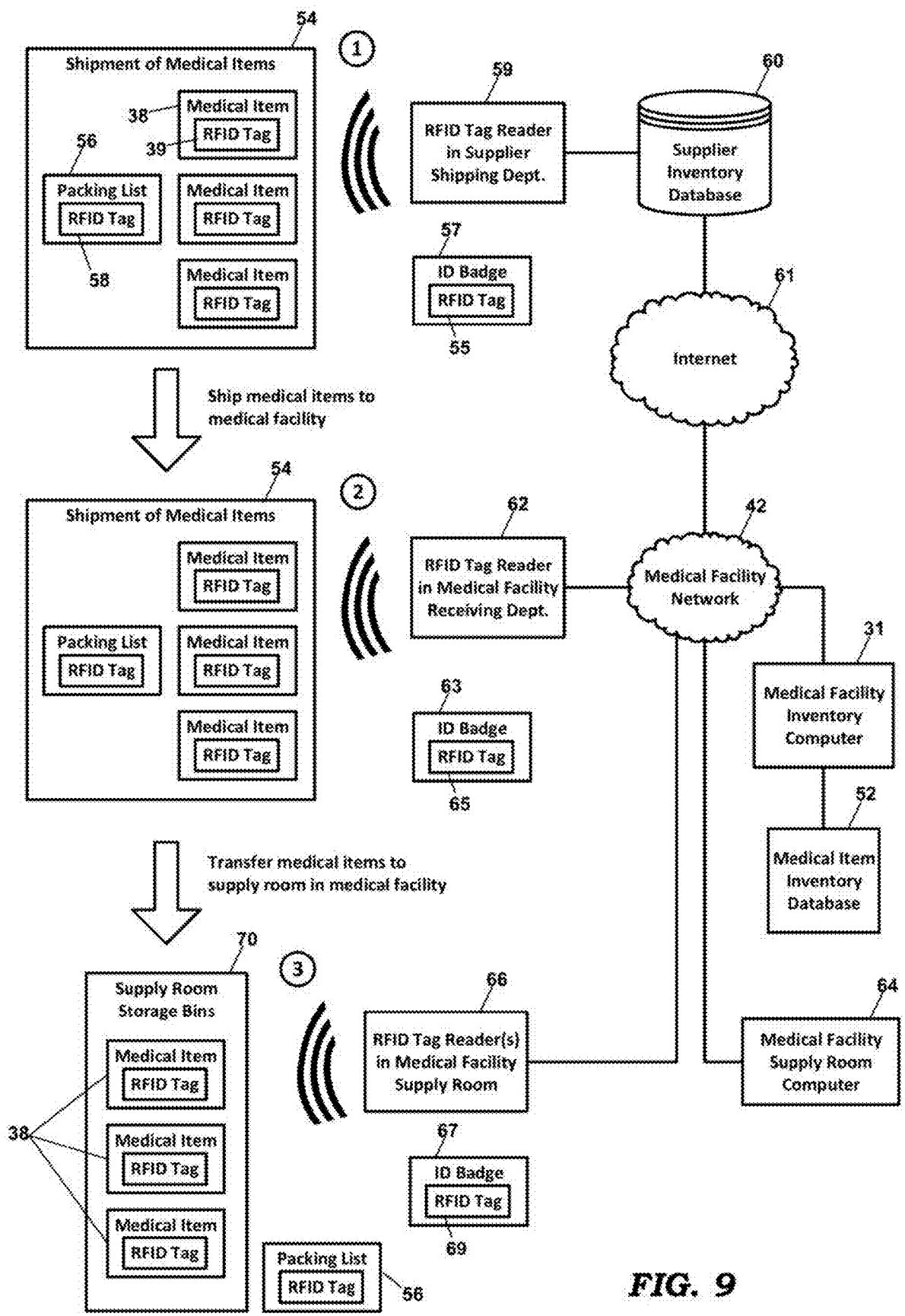
FIGS. 9-11 depict a system for tracking medical items through various transition points in a supply and consumption chain according to an embodiment of the invention.
Figure 10:
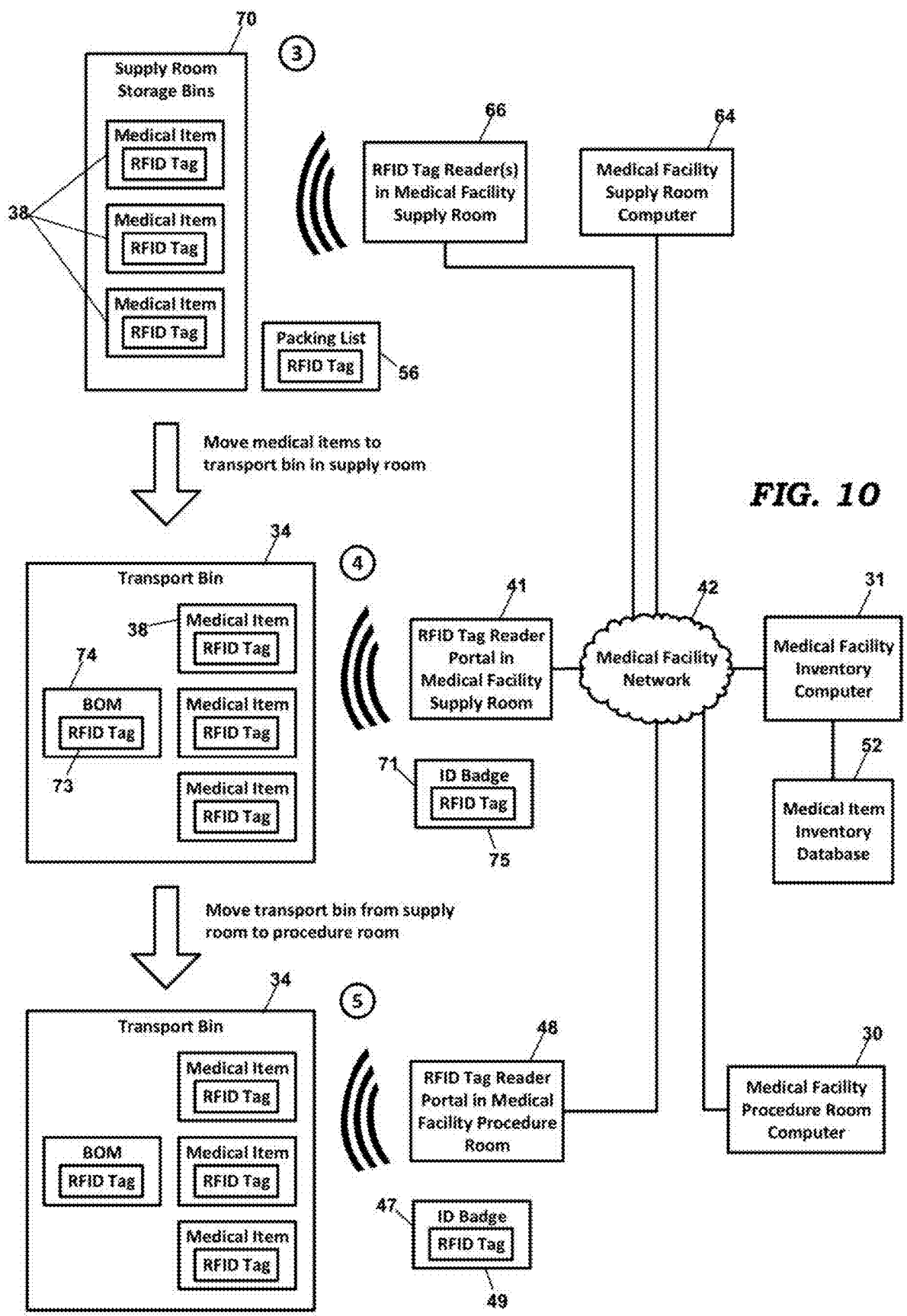
Figure 11:
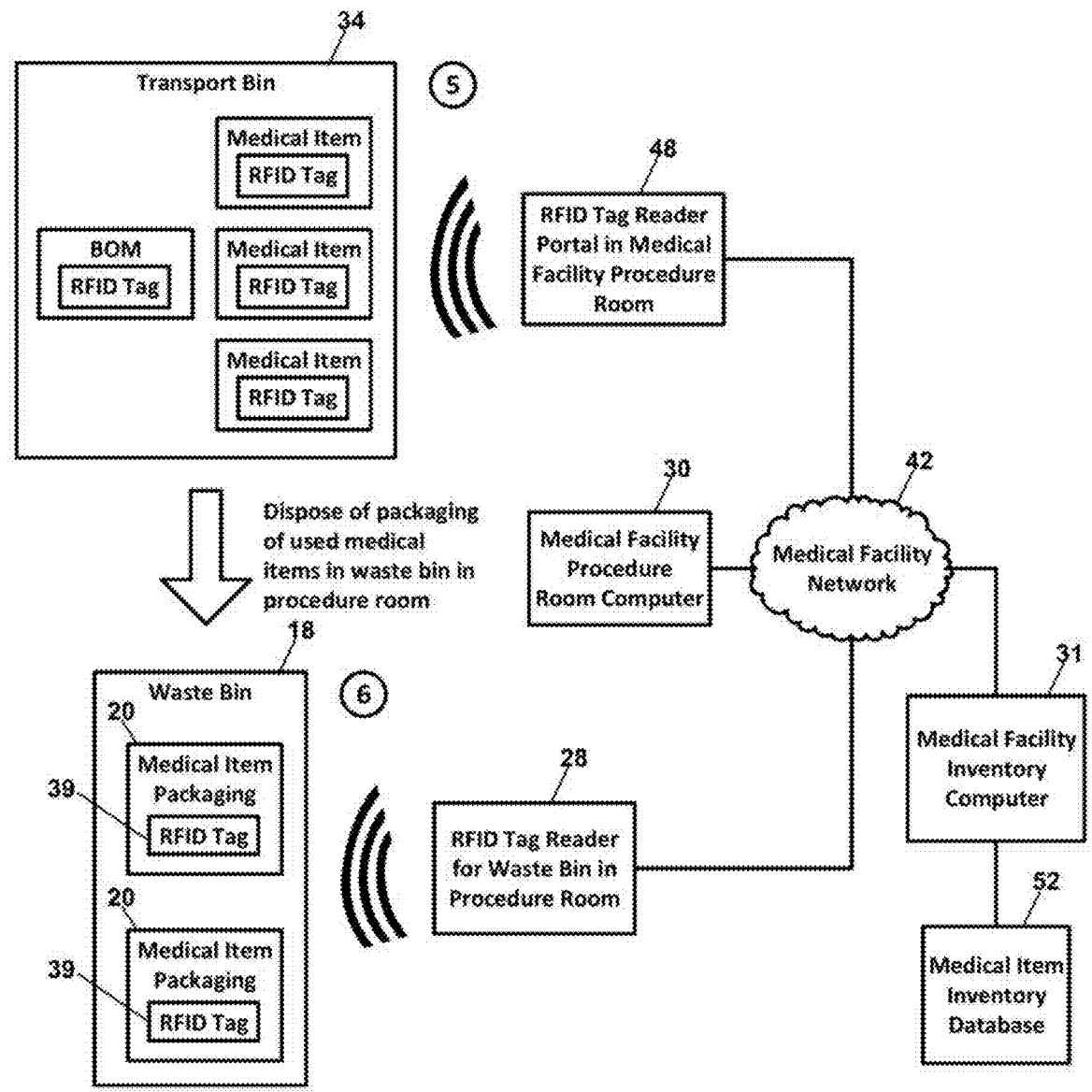

FIGS. 9-11 depict a system for tracking medical items through various transition points in a supply and consumption chain. As shown in FIG. 9, each shipment 54 of medical items 38 includes a packing list 56 that has a unique shipment identifier 58 encoded in an RFID tag and/or a bar code attached to the packing list. Upon packing of medical items 38 at a supplier facility for shipment (first transition point), a unique item identifier 39 encoded in an RFID tag and/or a bar code attached to each packed medical item 38 and the unique shipment identifier 58 of the accompanying packing list 56 are read by one or more reading devices 59 and are cross-referenced in a supplier inventory database 60. In preferred embodiments, the reading devices 59 may include one or more RFID tag readers and their associated antennas and one or more bar code readers. The one or more reading devices 59 may also read the unique personnel identifier 55 of the person responsible for the shipment of medical items at the supplier facility, which identifier may be encoded in the person's ID badge 57. In a preferred embodiment, the unique shipment identifier 58 is also cross-referenced in the supplier inventory database 60 with the unique personnel identifier 55. As the term is used herein, a "supplier facility" is any location at which the medical items are disposed prior to shipment to the medical facility, such as a manufacturer facility or a distributor facility.

Upon receipt of the shipment 54 of medical items at the medical facility (second transition point), the unique shipment identifier 58 of the packing list 56 is read and decoded by one or more reading devices 62, and the unique shipment identifier is stored in the medical facility inventory database 52 in association with a unique personnel identifier 65 of the person responsible for receiving the shipment of medical items at the medical facility. In preferred embodiments, the one or more reading devices 62 may include one or more RFID tag readers and their associated antennas and one or more bar code readers. The one or more reading devices 62 may also read the unique personnel identifier 65 of the person responsible for receiving the shipment of medical items at the medical facility, which identifier may be encoded in the person's ID badge 63.

Upon unpacking a received shipment 54 of medical items and placement into storage bins 70 in a supply room 68 at the medical facility (third transition point), the unique shipment identifier 58 and the unique item identifier 39 on each medical item 38 is read and decoded by one or more reading devices 66, and the unique item identifier 39 of each medical item 38 is stored in association with a unique supply room identifier in the inventory database 52 for the medical facility. In preferred embodiments, the one or more reading devices 66 may include one or more RFID tag readers and their associated antennas and one or more bar code readers. In preferred embodiments, the inventory database 52 also cross-references the unique item identifiers 39 with a unique personnel identifier 69 of the person responsible for placement of the medical items into inventory at the medical facility, which identifier may be encoded in the person's ID badge 67.

As shown in FIG. 10, upon pulling medical items 38 from the supply room storage bins 70 to be used in a medical procedure, examination or test, or to be otherwise dispensed to a patient (fourth transition point), the unique item identifier 39 on each medical item 38 is read and decoded by a portal reading device 41 in the supply room, and the unique item identifier of each medical item is stored in the inventory database 52 in association with a unique bill of material (BOM) identifier 73 of the BOM 74 for the procedure/exam/test. In a preferred embodiment, the unique item identifiers 39 and BOM identifier 73 is cross-referenced in the database 52 with a unique personnel identifier 75 of the person removing the medical items from the supply room, which identifier may be encoded in the person's ID badge 71. At this point, the medical items may be in a transport bin 34.

Upon delivery of the medical items 38 to a procedure room, examination room, or test room in the medical facility (fifth transition point), the unique item identifier 39 on each medical item is read and decoded by a portal reading device 48 in or at the entrance to the procedure/exam/test room, and the unique item identifier of each medical item is stored in the inventory database 52 in association with a unique procedure/exam/test room identifier and a unique personnel identifier 49 of a person accepting delivery in the procedure/exam/test room. The unique personnel identifier 49 may be encoded in the person's ID badge 47.

As shown in FIG. 11, upon dispensing the medical items 38 to a patient or otherwise consuming the medical items during a procedure or test performed on the patient in the procedure/exam/test room (sixth transition point), the unique item identifier 39 on the packaging 20 of each used medical item is read and decoded by a reading device 28 associated with the waste bin 18 in the supply room, and the unique item identifier of each medical item is stored in the inventory database 52 in association with a unique patient identifier.

The medical items 38 that are not used or consumed during the medical procedure are preferably placed back into the transport bin 34, the transport bin 34 is passed through the portal 48, and the reader 46 reads the RFID tags of the unused items 38. In a preferred embodiment, the item identification information encoded in those RFID tags is cross-referenced in the database 52 with a unique personnel identifier of the person removing the unused medical items from the medical procedure room and transporting the items to the supply room for restocking, which identifier may be encoded in the person's ID badge.

At each transition point, a prompt may be automatically generated to remind the responsible personnel to scan the unique item identifier 39 on each medical item 38 so that the information will be entered into the inventory database 52, or to remind the responsible personnel to take other action as may be necessary based on the location and status of the medical items 38. These prompts may be visual or audible.

In this preferred embodiment, the inventory database 52 maintains a chain of custody for each item 38 through each transition point (and for each shipment 54 of items between the first and second transition points) and keeps records of the personnel responsible for each item or shipment at each location at any particular time.

At some transition points, individual medical item information may not be specifically recorded, although bulk information associated with the packing list 56 will be recorded. When the medical items are dispensed to the subsequent transition point, the unique item identifiers 39 may recovered and the unique item identifier information can be automatically associated with the dispensing activity where unique item identifier information was previously not recorded.

Although a particular sequence of transition points is described, transition points could consist of any handling point along the supply chain for a medical item from manufacturer to patient.

In further embodiments, each transition point is defined by the type of location. Each type of location may have a set of characteristics associated with that location type that trigger certain action prompts when the medical items are associated with that particular location type in the database 52. For example, when the shipment 54 of medical items is received at a supply room 68, such as by scanning the identification information on a packing list 56, the supply room identification equipment may prompt the inventory management personnel to place the products in the appropriate product storage location, initiate an RFID scan of the room to identify the medical items present in the room and subsequently present information to the inventory management personnel to determine if the room inventory, as updated, reconciles with the packing list.

In another example, when the RFID reader 48 in a procedure/examination room detects in the room a medical item that is considered to be Durable Medical Equipment, Prosthetics, Orthotics and Supplies (DMEPOS, also collectively referred to herein simply as "DME"), and it also detects a patient identification number encoded in an RFID tag associated with a particular patient in the room, the procedure room computer 30 may generate action prompts based on association of the DME item with the patent. For example, the procedure room computer 30 may prompt the treating personnel to disclose to the patient certain information related to the proper use of the DME item, to input information to verify the delivery of the DME item to the patient, or to obtain the patient's signature to acknowledge receipt of the DME item. In a situation in which an old or used DME item is detected in the room, and the patient is supposed to receive a new item, the system may generate a notification to treating personnel that the old/used item should go back to hospital stock and a new item should be dispensed to patient.

In some embodiments, the exits of the hospital or other medical facility are transition points at which networked RFID tag readers are positioned. When a just-dispensed DME item is detected at any of these exit transition points, the medical item inventory computer 31 triggers a billing change event to cause the billing for the DME item to change from Medicare Part A, in which the medical facility pays for rental, to Medicare Part B, in which the patient or the patient's insurance company is billed for the item. This exit event may also cause the medical item inventory computer 31 to update the chain of custody for the DME item to indicate a transfer of possession from the medical facility to the patient. Such an exit event may also trigger the sending of notifications to the patient and medical personnel regarding follow-up care for patient using the DME item, such as notifications recommending a Part B healthcare provider and prompting the scheduling of follow-up appointments.

Medical Item Supply Room

Figure 12:
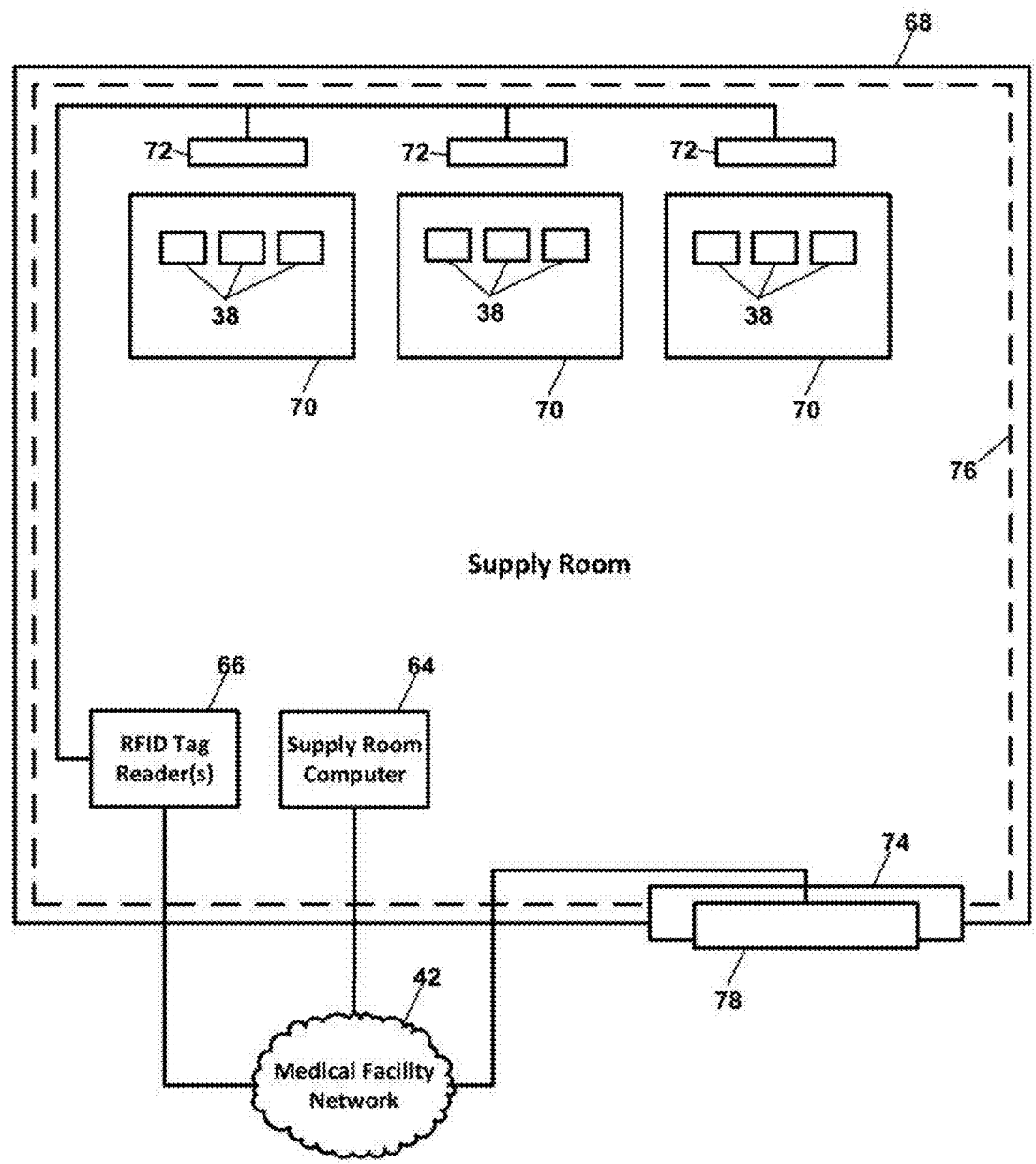
FIG. 12 depicts an apparatus for maintaining an inventory of medical items according to an embodiment of the invention.

FIG. 12 depicts a functional block diagram of features of a medical item supply room 68 according to a preferred embodiment. Within the supply room 68 are one or more storage bins 70 in which medical items 38 are stored until they are needed for treatment of a patient. As the term is used herein, a "storage bin" is any storage structure in or on which medical items may be stored, including but not limited to a container, shelf, drawer, hanger, or cabinet. One or more RFID antennas 72 are directed toward the storage bins 70 to detect RFID tags on medical items 38 stored therein. The antennas 72 are electrically connected to one or more RFID tag readers 66 that are in communication with the medical facility network 42. In some embodiments, a supply room computer 64 is provided to allow personnel in the supply room 68 to access medical item inventory information over the network 64.

In some embodiments, the supply room 68 has RF shielding 76 in the walls, floor and ceiling to prevent detection of RFID tags that are outside the supply room. RFID shielding 76 may also be provided in gaskets around the edges of the door frame and in a door sweep on the bottom of the door.

Figure 13:
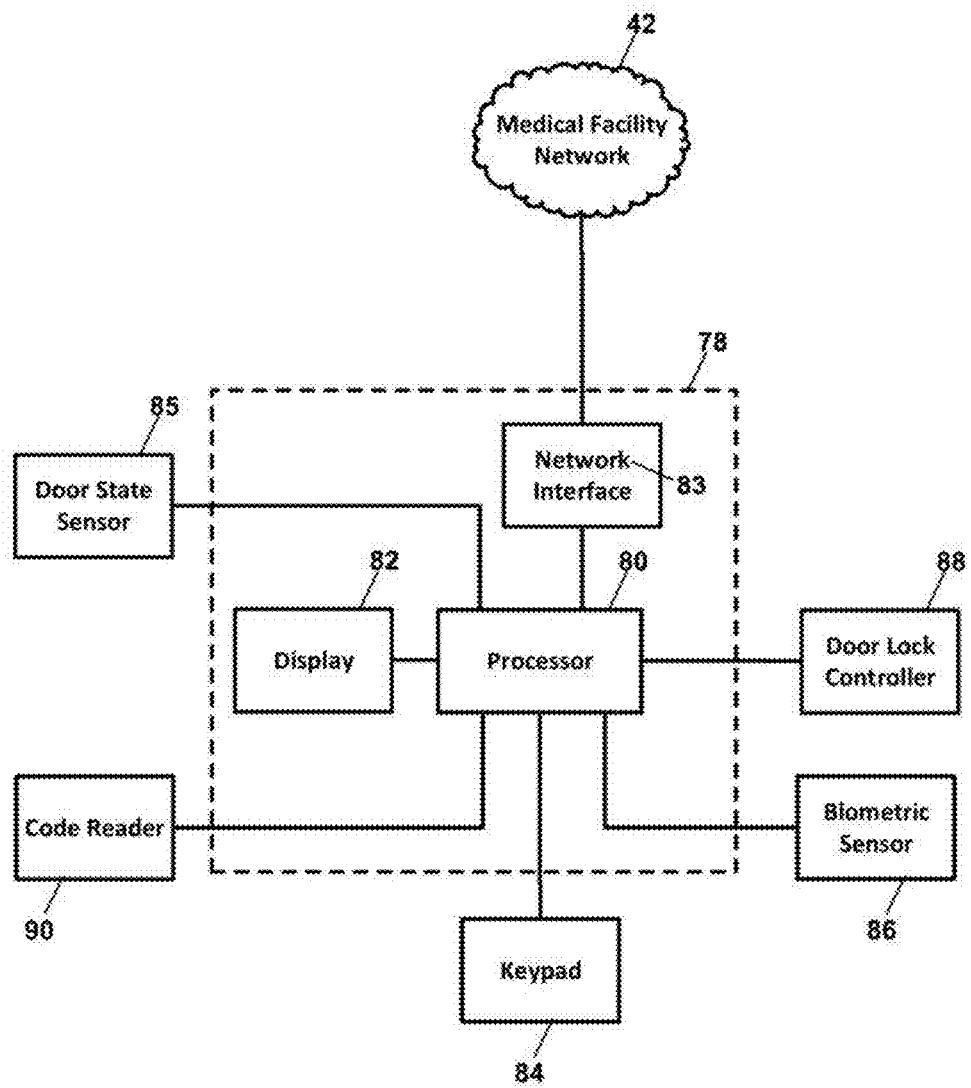
FIG. 13 depicts a computer system associated with a supply room door according to an embodiment of the invention.

In some embodiments, a computer 78 is built into the door 74 of the medical item supply room 68. As shown in FIG. 13, this computer 78 preferably includes a processor 80, a touch screen display 82, keypad 84, biometric sensor 86 such as a fingerprint reader or retinal scanner, and a code reader 90, such as an RFID reader, barcode reader or magnetic stripe reader, for reading identification information of personnel seeking access to the supply room and decoding the unique personnel identifiers encoded personnel ID badges. In a preferred embodiment, the processor 80 interfaces with one or more sensors 85 that sense whether the door 74 is in an open state or a closed state and/or whether the door is locked or unlocked.

The computer 78 may also interface with a door lock controller 88 to allow or deny access to the room based on the identity of the person seeking access and based on ongoing activities in the room. For example, if another person is in the room entering items into inventory, the computer may be programmed to not allow access so as not allow outside RFID signals into the room and interfere with the ongoing inventory activity. The computer 78 may also be programmed to keep the door locked while an RFID scan is taking place, whether or not anyone is in the room. The computer 78 may also be programmed to deactivate the RFID reader 66 inside the room when the door is open so that no RFID tags on items outside the room will be detected.

In some embodiments, the supply room computer 64 or the computer 78 controls the RFID tag reader(s) 66 to perform an RFID antenna calibration procedure. This procedure may involve placing a known number of RFID-tagged items in various different storage bins 70 in the supply room 68 with the RFID tag reader 66 initially deactivated. The computer 64 then activates the RFID tag reader 66 at a first relatively low transmitter power level and the number of tags detected is noted. If not all the tags present in the room were detected, the transmitter power level is increased by a small amount to a second power level that is greater than the first power level and the number of tags detected is noted. This procedure is repeated until all tags are detected, and the lowest transmitter power level at which all tags were detected is stored as the optimum operational level. This general procedure could also be performed by starting at a relatively high transmitter power level at which all tags are detected and then stepping down in power until not all of the tags are detected.

UDI Fraud Detection.

Figure 14:
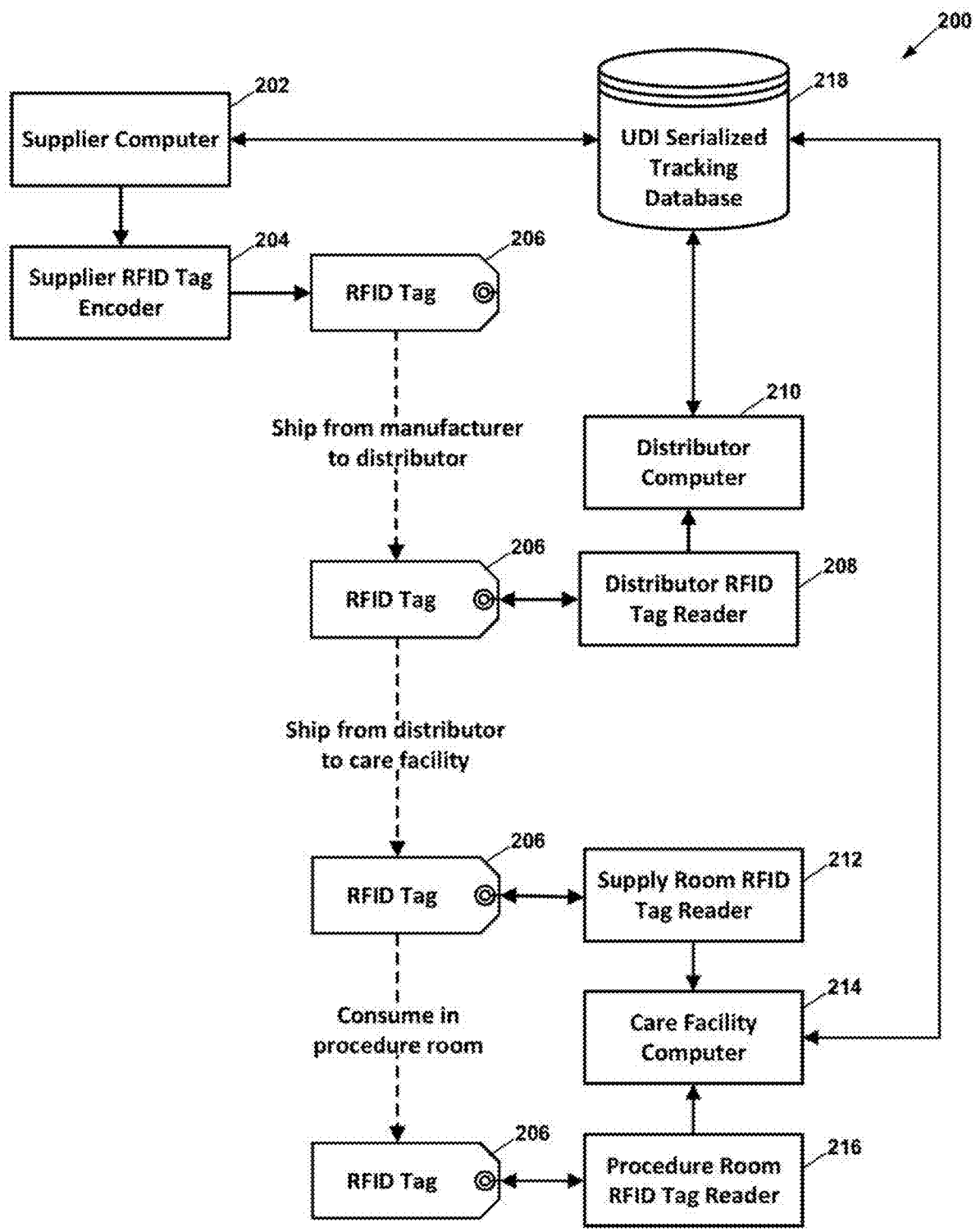
FIG. 14 depicts a system for detecting fraud in the reporting of usage of medial items in the treatment of medical patients according to an embodiment of the invention.
Figure 15:
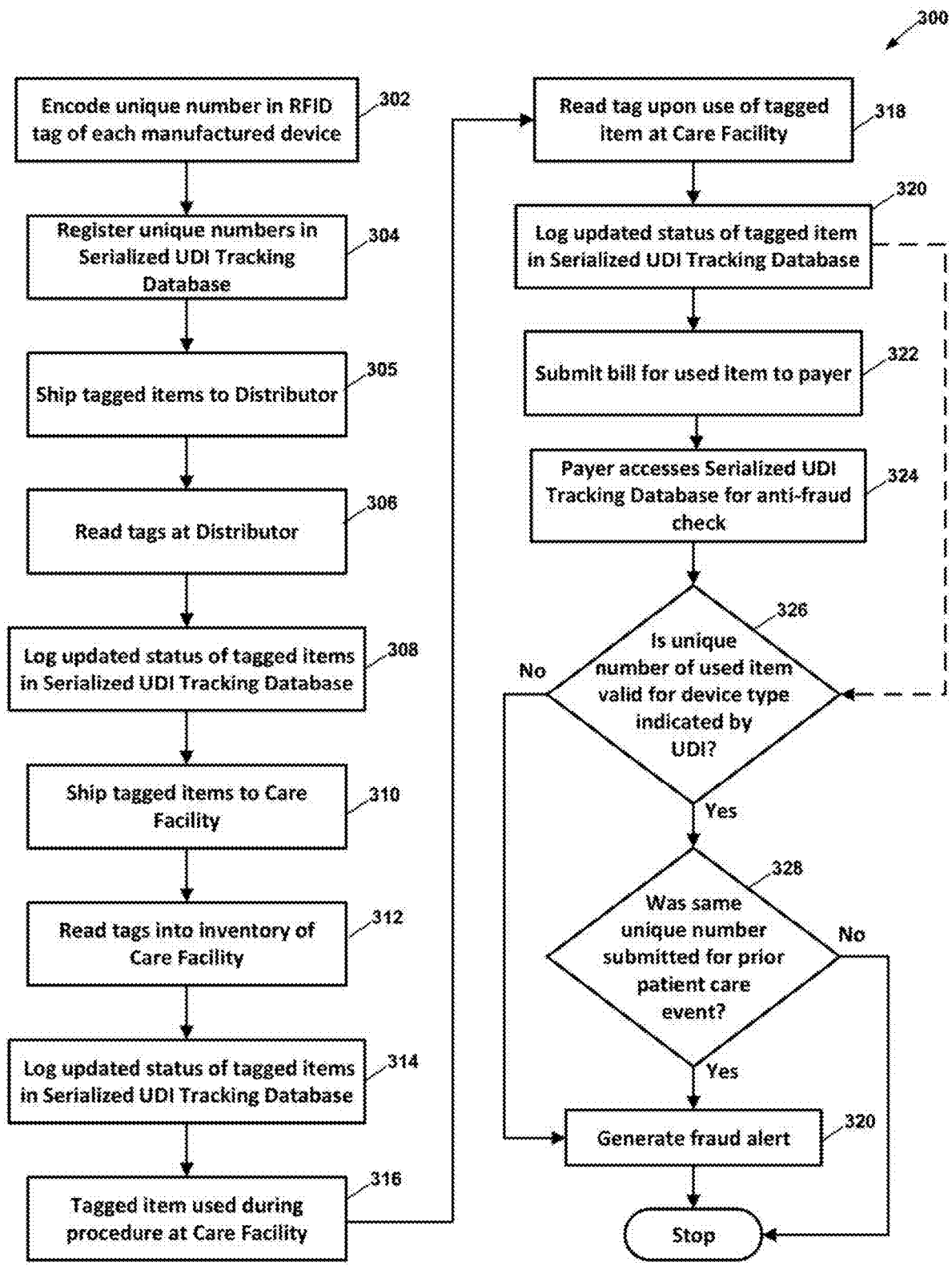
FIG. 15 depicts a method for detecting fraud in the reporting of usage of medial items in the treatment of medical patients according to an embodiment of the invention.

FIG. 14 depicts a preferred embodiment of a system 200 for detecting fraud in the reporting of usage of medical items in the treatment of medical patients, and FIG. 15 depicts a process performed by the system of FIG. 14 to detect and report such fraud. The system 200 includes a supplier inventory computer 202 in communication with a supplier RFID tag encoder 204, both of which are disposed at a supplier facility. The system 200 also includes a distributor inventory computer 210 in communication with a distributor RFID tag reader 208, both of which are disposed at a distributor facility. A medical care facility inventory computer 214 is in communication with a supply room RFID tag reader 212 and a procedure room RFID tag reader 216, all of which are disposed at a medical care facility. As shown in FIG. 1, one embodiment of the procedure room RFID tag reader 216 is the tag reader 28 connected to the antennas 14a-14b in the shielded enclosure 12 disposed in a medical procedure room. Another embodiment of the procedure room RFID tag reader 216 is the tag reader 46 connected to the antennas 50a-50d in the portal 48. The supplier inventory computer 202 and the medical care facility inventory computer 214 are in communication with a UDI Serialized Tracking Database 218. In a preferred embodiment, the database 218 is maintained at the facility of a third party UDI fraud detection service provider.

The medical item supplier assigns each individual instance of a medical item a unique identification number (e.g. GS1, SGTIN, EPC, etc.) that is encoded in an RFID tag 206 attached to the device or its packaging. For example, if twenty items having the same Device Identifier (DI) are manufactured in the same lot/batch, each of the twenty items has a different unique identification number encoded in an attached RFID tag. The unique identification number is preferably encoded in the RFID tag 206 for each item at the time of manufacture using the tag encoder 204 (step 302 in FIG. 15). Preferably, RFID chip security is utilized to lock the RFID tag 206 after programming to prevent the unique identification number on the tag from being modified. As an option in some embodiments, the unique identification number is also visually displayed on the packaging and encoded in a barcode on the packaging.

The unique identification number encoded in the RFID tag 206 is assigned to the corresponding UDI (i.e. DI and PI) for the particular medical item and is registered with the UDI fraud detection service provider for storage in the UDI Serialized Tracking Database 218 (step 304). Preferably, this registration process is performed at the time of manufacture.

The tagged medical items are shipped from the supplier to the distributor (step 305), and the tags on incoming items are read at the distributor facility using the distributor RFID tag reader 208 (step 306). The distributor computer 210 then communicates with the UDI Serialized Tracking Database 218 to update the status of the tagged medical items (step 308).

After the medical items are shipped from the distributor to the medical care facility (step 310), the tags on the incoming items are read using the supply room RFID tag reader 212 (step 312). The care facility computer 214 then communicates with the UDI Serialized Tracking Database 218 to update the status of the tagged medical items (step 314).

When a medical item is used during a procedure to treat a patient (step 316), the unique identification number of the item is logged by scanning the RFID tag attached to or embedded in the item or its wrapper using the RFID tag reader 216 in the procedure room (step 318). In preferred embodiments described herein, the RFID tags on item wrappers are automatically read when the wrappers are dropped into the shielded enclosure 12 (FIG. 1). In alternative embodiments, the RFID tags on or embedded in item wrappers are automatically read when the wrappers pass through the portal 48. The care facility computer 214 then communicates with the UDI Serialized Tracking Database 218 to update the status of the tagged medical items (step 320). Using this information, the UDI fraud detection service provider can track the status (i.e., used in patient care or not yet used in patient care) of each individual instance of each medical item.

At some point after the procedure, the medical care provider submits the unique identification numbers encoded in the RFID tags 206 of used items in a bill to a payer (step 322). The bill payer, or any other entity wishing to validate that the devices listed on bills were actually used during patient care, may access the UDI Serialized Tracking Database 218 such as via a dedicated website to perform an anti-fraud check (step 324). In a preferred embodiment, such a check involves two steps: (a) checking that the submitted unique identification number is valid for the UDI (e.g. that the unique number submitted for a scalpel is a valid unique number for a scalpel)(step 326), and (b) validating that the same unique number has not been submitted more than once based on treatment of two different patients (step 328). If the unique identification number of a used medical item is not valid for the device type indicated by the UDI (step 326), a fraud alert message is generated (step 330). A fraud alert message is also generated if the unique identification number has been submitted previously in association with a prior patient care event (step 328). Fraud alert messages may be provided in the form of emails, text messages, notifications on a UDI fraud check website screen, or by other forms of electronic messaging.

In some embodiments, an automatic fraud check is triggered based on the reading of an RFID-tagged wrapper dropped into the shielded enclosure (step 318) and the logging of the decoded unique identification number into the database 218. This automatic fraud check (indicated by the dashed line in FIG. 15) preferably occurs independently of the submission of a bill to a payer. Thus, the automatic fraud check may find potential problems even before a bill is submitted to a payer. For example, during the automatic fraud check, it may be determined at step 328 that the unique identification number for the used item matches the unique identification number of an item that was logged previously into the database 218 as being used in a procedure. Since it is not possible for the same consumable item to have been used twice, the first "use" of the item must have been logged fraudulently in order to inflate a bill. This information can be used to investigate the first logged "use" to either track down the perpetrator of the fraud or to determine whether a mistake was made due to negligence or carelessness rather than an intentionally fraudulent act.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. An apparatus for recording consumption of medical items used during performance of a medical procedure in a medical facility and for detecting fraud in reporting the consumption of the medial items, wherein RFID tags are attached to the medical items or the medical items are at least initially enclosed in wrappers having RFID tags disposed in or on the wrappers, wherein a unique identification number that uniquely identifies an individual medical item is encoded in each of the RFID tags, the apparatus comprising:
    a database in which are stored:
        Unique Device Identifier (UDI) numbers assigned by a governmental agency to identify specific types of medical items used in medical procedures; and
        unique identification numbers encoded in the RFID tags, wherein each unique identification number is stored in the database in association with one of the UDI numbers that identifies the specific type of medical item identified by the unique identification number;
    one or more RFID antennas for receiving radio frequency signals emanated from RFID tags associated with medical items that have been consumed during performance of the medical procedure, wherein the radio frequency signals contain the unique identification numbers encoded in the RFID tags;
    an RFID reader electrically connected to the one or more RFID antennas, the RFID reader for decoding the unique identification numbers contained in the radio frequency signals emanated from the RFID tags; and
    a computer that is in communication with the database, the computer having a processor that executes instructions for:
        (a) receiving the unique identification numbers decoded by the RFID reader;
        (b) upon receipt of the unique identification numbers decoded by the RFID reader, accessing the UDI numbers and the unique identification numbers stored in the database;
        (c) generating a fraud alert message if any of the unique identification numbers decoded by the RFID reader for each medical item is not associated in the database with a UDI number assigned to identify the specific type of medical item identified by the unique identification number; and
        (d) generating a fraud alert message if any unique identification number decoded by the RFID reader matches a unique identification number stored in the database in association with a medical item that was previously consumed in medical treatment of a patient.

2. The apparatus of claim 1 wherein the computer is disposed in the medical facility and is in electrical communication with the RFID reader.

3. The apparatus of claim 1 wherein the computer is used by a medical bill payer entity that receives a bill listing the unique identification numbers decoded by the RFID reader.

4. A method for recording consumption of medical items used during performance of a medical procedure and for detecting fraud in reporting the consumption of the medial items, wherein RFID tags are attached to the medical items or the medical items are at least initially enclosed in wrappers having RFID tags disposed in or on the wrappers, wherein a unique identification number that uniquely identifies an individual medical item is encoded in each of the RFID tags, the apparatus comprising:
    (a) storing in a database:
        Unique Device Identifier (UDI) numbers assigned by a governmental agency to identify specific types of medical items used in medical procedures; and
        unique identification numbers encoded in the RFID tags, wherein each unique identification number is stored in the database in association with one of the UDI numbers that identifies the specific type of medical item identified by the unique identification number;
    (b) receiving radio frequency signals emanated from RFID tags associated with medical items that have been consumed during performance of the medical procedure, wherein the radio frequency signals contain the unique identification numbers encoded in the RFID tags;

(c) decoding the unique identification numbers contained in the radio frequency signals emanated from the RFID tags;

(d) accessing the UDI numbers and the unique identification numbers stored in the database;

(e) generating a fraud alert message if any of the unique identification numbers decoded from the radio frequency signals is not associated with a UDI number assigned to identify the specific type of medical item identified by the unique identification number; and (f) generating a fraud alert message if any of the unique identification numbers decoded from the radio frequency signals matches a unique identification number stored in the database in association with a medical item that was previously consumed during medical treatment of a patient.

5. The method of claim 4 wherein steps (d), (e) and (f) are performed by a computer that is disposed in the medical facility and is in electrical communication with the RFID reader, and wherein steps (d), (e) and (f) are performed automatically upon completion of step (c).

6. The method of claim 4 wherein steps (d), (e) and (f) are performed by a computer that is used by a medical bill payer entity that receives a bill listing the unique identification numbers decoded by the RFID reader, and wherein steps (d), (e) and (f) are performed upon entry into the computer of the unique identification numbers listed in the bill.

7. An apparatus for recording consumption of medical items used during performance of a medical procedure in a medical facility and for detecting fraud in reporting the consumption of the medial items, wherein RFID tags are attached to the medical items or the medical items are at least initially enclosed in wrappers having RFID tags disposed in or on the wrappers, wherein a unique identification number that uniquely identifies an individual medical item is encoded in each of the RFID tags, the apparatus comprising:

a database in which are stored:

Unique Device Identifier (UDI) numbers assigned by a governmental agency to identify specific types of medical items used in medical procedures; and unique identification numbers encoded in the RFID tags, wherein each unique identification number is stored in the database in association with one of the UDI numbers that identifies the specific type of medical item identified by the unique identification number;

one or more RFID antennas for receiving radio frequency signals emanated from RFID tags associated with medical items that have been consumed during performance of the medical procedure, wherein the radio frequency signals contain the unique identification numbers encoded in the RFID tags;

an RFID reader electrically connected to the one or more RFID antennas, the RFID reader for decoding the unique identification numbers contained in the radio frequency signals emanated from the RFID tags; and a computer that is in communication with the database and has a processor that executes instructions for:

accessing the UDI numbers and the unique identification numbers stored in the database;

generating a fraud alert message if any of the unique identification numbers decoded by the RFID reader for each medical item is not associated with a UDI number assigned to identify the specific type of medical item identified by the unique identification number; and generating a fraud alert message if any unique identification number decoded by the RFID reader matches a unique identification number stored in the database in association with a medical item that was previously consumed in medical treatment of a patient.

8. The apparatus of claim 7 wherein the computer is disposed in the medical facility and is in electrical communication with the RFID reader.

9. The apparatus of claim 7 wherein the computer is used by a medical bill payer entity that receives a bill listing the unique identification numbers decoded by the RFID reader.

\* \* \* \* \*